United States Patent [19]
Charlton et al.

[11] Patent Number: 6,015,834
[45] Date of Patent: Jan. 18, 2000

[54] IN VIVO TREATMENT OF MAMMALIAN CELLS WITH A CELL MEMBRANE PERMEANT CALCIUM BUFFER

[75] Inventors: Milton P. Charlton, Toronto; Michael Tymianski, Willowdale, both of Canada

[73] Assignee: Toronto Neuroprotection Group, Toronto, Canada

[21] Appl. No.: 07/963,676

[22] Filed: Oct. 20, 1992

[51] Int. Cl.$^7$ .................................................. A61K 31/195
[52] U.S. Cl. ............................................................ 514/561
[58] Field of Search ............................................ 514/561

[56] References Cited

U.S. PATENT DOCUMENTS

| | | | |
|---|---|---|---|
| 4,806,604 | 1/1989 | Tsien et al. | 549/7 |
| 5,049,673 | 9/1991 | Tsien et al. | 546/107 |
| 6,141,627 | 9/1992 | Tsien et al. | 204/157.88 |

OTHER PUBLICATIONS

Neisen C, Charlton MP, Carlen PL (1991), "Postsynaptic and Presynaptic Effects of the Calcium Chelator BAPTA on Synaptic Transmission in Rat Hippocampal Dentate Granule Neurons." Brain Res 555:319–325.

Caprenter–Deyo L, et al (1991), "Toxicity to Isolated Hepatocytes Caused by the Intracellular Calcium Indicator, Quin 2." J. Pharmacol Exp Therapeut 258:739–746.

K.G. Baimbridge and K.M. Abdel–Hamid, Intra_Neuronal Ca2+ Buffering with BAPTA Enhances Glutamate Excitotoxicity In Vitro and Ischemic Damage In Vivo, Society for Neuroscience Abstracts, 18, 1992, 571.4, 22nd Annual Meeting, Anaheim, California, Oct. 25–30, 1992.

Scharfman He, and Schwartzkroin PA, "Protection of Dentate Hilar Cells from Pronlonged Stimulation by Intracellular Calcium Chelation." *Science* @$¢:257–260, (1989).

Billman GE, et al (1991), "Elevated Myocardial Calcium and Its Role in Sudden Cardiac Death." *FASEB J.* 5:2586–2592.

Tyminaski M. and Tator C.H. "A Novel Approach to Prventing Ca2+ Neurotoxicity Iwth Membrane_Premeant Calcium Chelators", The Canadian Journal of Neurological Sciences, #2, 19, May, 1992.

*Primary Examiner*—Raymond Henley, III
*Attorney, Agent, or Firm*—Pillsbury Madison & Sutro, LLP

[57] ABSTRACT

A method of reducing the damaging effect of an injury to mammalian cells by treatment of the cell or mammalian tissue in vivo with a cell membrane permeant calcium buffer. The method comprises treating mammalian tissue with a damage reducing effective amount of the calcium buffer, preferably, a BAPTA derivative. The method may be used to control the concentration of $Ca^{2+}$ ions in the vicinity of ion channel pores of the cells to prevent diffusion of toxic amounts of $Ca^{2+}$ ions to subcellular sites located near the source of $Ca^{2+}$ influx. The buffer treatment may be applied as a prophylactic or after the mammalian tissue has sustained injury.

16 Claims, 9 Drawing Sheets

FIG. I

FIG. 2
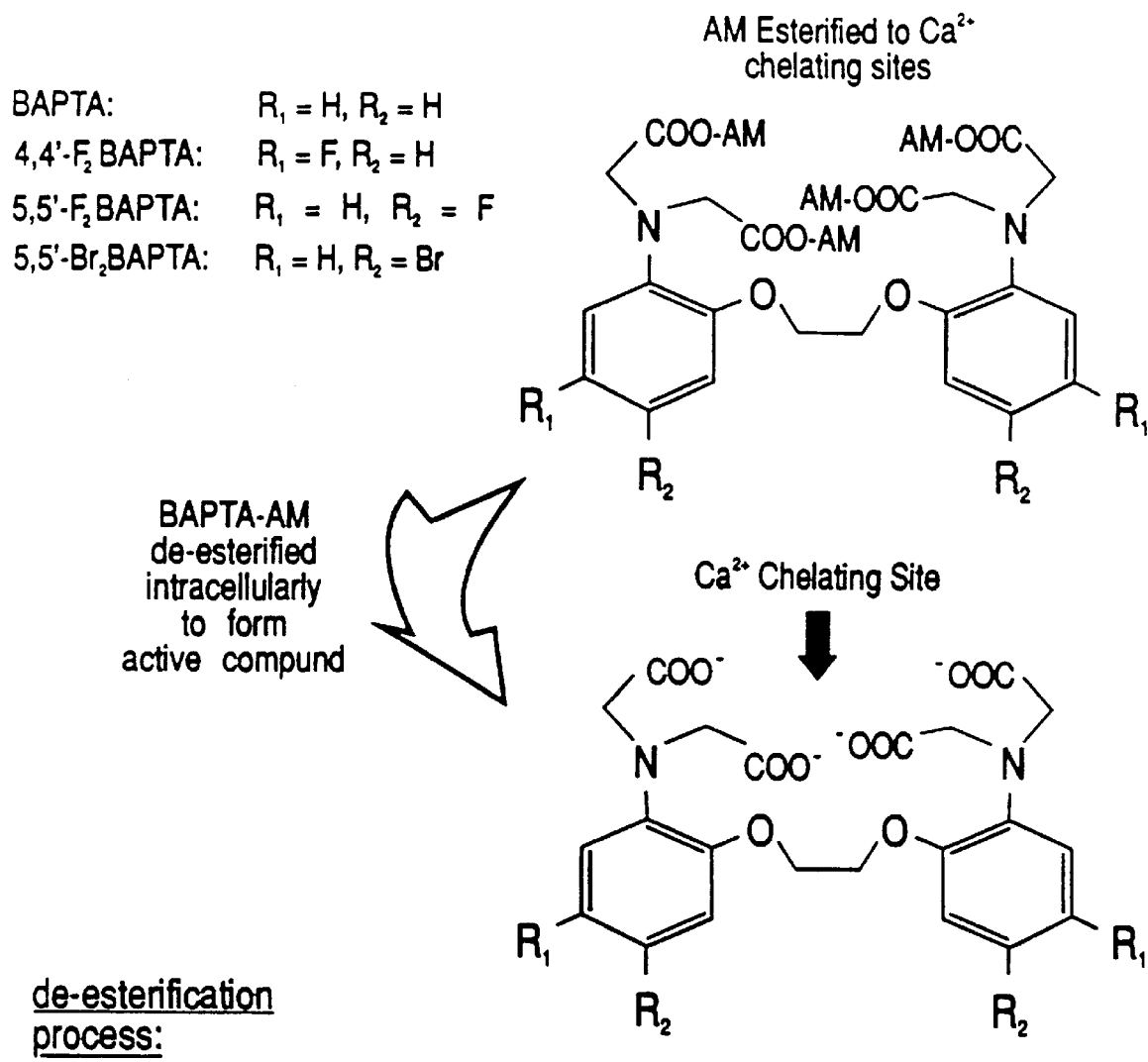
de-esterification process:
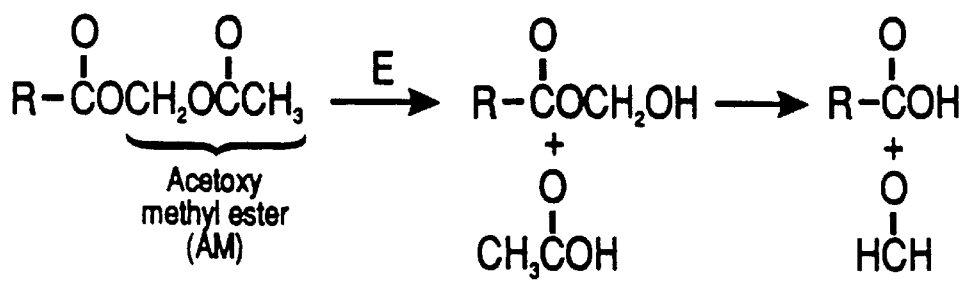
E = intracellular esterase

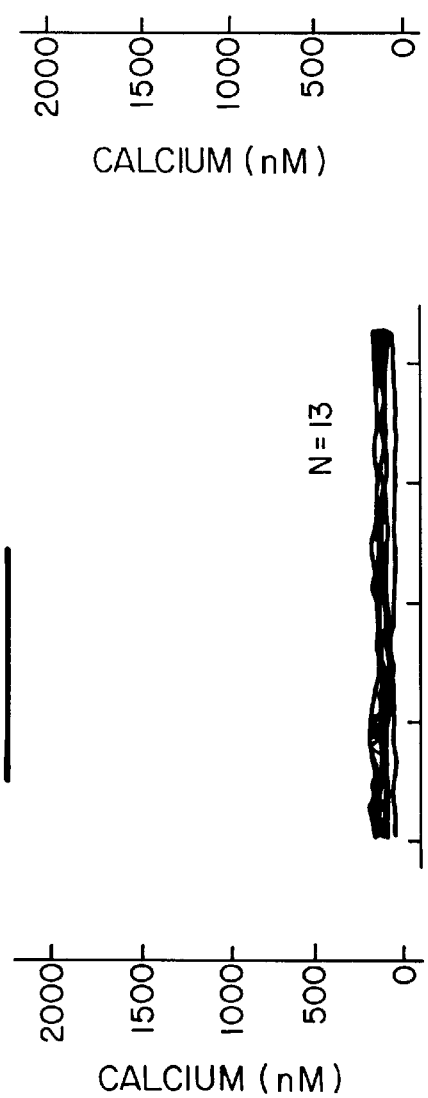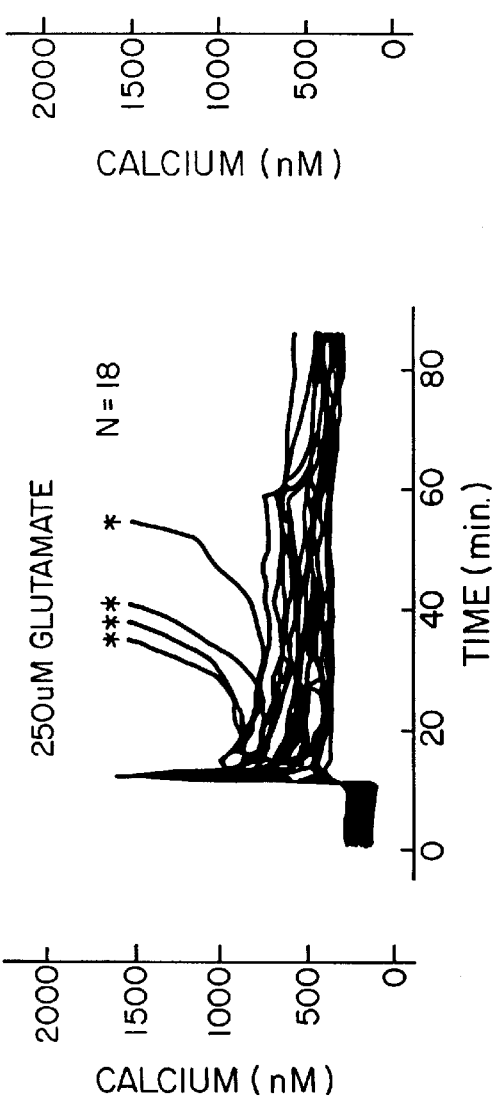

RAT NO. 4   RAT NO. 6

IN VIVO TREATMENT OF MAMMALIAN CELLS WITH A CELL MEMBRANE PERMEANT CALCIUM BUFFER

FIELD OF THE INVENTION

This invention relates to a method of reducing the damaging effect of an injury to mammalian cells by treatment with a cell membrane permeant calcium buffer; said calcium buffers per se and pharmaceutical compositions comprising said calcium buffers.

BACKGROUND TO THE INVENTION

Ischemic or traumatic injuries to the brain or spinal cord often produce irreversible damage to central nervous system (CNS) neurons and to their processes. These injuries are major problems to society as they occur frequently, the damage is often severe, and at present there are still no effective treatments for acute CNS injuries. Clinically, ischemic cerebral stroke or spinal cord injuries manifest themselves as acute deteriorations in neurological capacity ranging from small focal defects-, to catastrophic global dysfunction-, to death. It is currently felt that the final magnitude of the deficit is dictated by the nature and extent of the primary physical insult, and by a time-dependent sequence of evolving secondary phenomena which cause further neuronal death. Thus, there exists a theoretical time-window, of uncertain duration, in which a timely intervention might interrupt the events causing delayed neurotoxicity. However, little is known about the cellular mechanisms triggering and maintaining the processes of ischemic or traumatic neuronal death, making it difficult to devise practical preventative strategies. consequently, there are currently no clinically useful treatments for cerebral stroke or spinal cord injury.

In vivo, a local reduction in CNS tissue perfusion mediates neuronal death in both hypoxic and traumatic CNS injuries. Local hypoperfusion is usually caused by a physical disruption of the local vasculature, vessel thrombosis, vasospasm, or luminal occlusion by an embolic mass. Regardless of its etiology, the resulting ischemia is believed to damage susceptible neurons by impacting adversely on a variety cellular homeostatic mechanisms. Although the nature of the exact disturbances is poorly understood, a feature common to many experimental models of neuronal injury is a rise in free intracellular calcium concentration ($[Ca^{2+}]_i$). Neurons possess multiple mechanisms to confine $[Ca^{2+}]_i$ to the low levels (about 100 nM)-necessary for physiological function. It is widely believed that a prolonged, rise in $[Ca^{2+}]_i$ deregulates tightly-controlled $Ca^{2+}$-dependent processes, causing them to yield excessive reaction products, to activate normally quiescent enzymatic pathways, or to inactivate regulatory cytoprotective mechanisms. This, in-turn, results in the creation of experimentally observable measures of cell destruction such as lipolysis, proteolysis, cytoskeletal breakdown, pH alterations, and free radical formation.

The classical approach to preventing $Ca^{2+}$ neurotoxicity has been through pharmacological blockade of $Ca^{2+}$ entry through $Ca^{2+}$ channels and/or of excitatory amino acid (EAA)-gated channels. Variations on this strategy often lessen EAA-induced or anoxic cell death in vitro, lending credence to the $Ca^{2+}$-neurotoxicity hypothesis. However, a variety of $Ca^{2+}$ channel- and EAA-antagonists fail to protect against neuronal injury in vivo, particularly in experimental Spinal Cord Injury (SCI), head injury, and global cerebral ischemia. It is unknown whether this is due to insufficient drug concentrations, inappropriate $Ca^{2+}$ influx blockade, or to a contribution from non-$Ca^{2+}$ dependent neurotoxic processes. It is likely that $Ca^{2+}$ neurotoxicity is triggered through different pathways in different CNS neuron types. Hence, successful $Ca^{2+}$-blockade would require a polypharmaceutical approach.

It is well-known that calcium buffer salts and their acetoxymethyl esters have been used extensively to study various aspects of cellular neurophysiology. These studies have focused primarily on experiments involving isolated tissue preparations in vitro.

Kudo et al, Brain Research, 528, (1990), pp 48–54, describe the treatment of an in vitro amphibian neuronal preparation with Quin-2, membrane permeant calcium buffer, used to indicate the presence of calcium ions by fluorescence, for the purposes of determining the effect of this buffer upon intracellular calcium concentration, and resistance to excessive electrical stimulation under the application of the neurotoxin L-glutamate-sodium and the calcium ionophore A23187, a compound which makes the cell membrane permeable to the calcium ion.

Scharfman and Schwartzkroin, Science, 246, Oct. 13 (1989), pp 257–260, describe experiments in vitro that demonstrate that single neurons that have calcium binding proteins were more resistant to excessive electrical stimulation. Neurons with less calcium binding proteins were less resistant to excessive stimulation. Neurons with no calcium binding proteins into which a salt of a $Ca^{2+}$ buffer was injected by micro-pipette became more resistant to excessive electrical stimulation than neurons into which the $Ca^{2+}$ buffer was not injected. The authors concluded that effective buffering of intracellular calcium during periods of excessive excitation is crucial to neuronal survival. A further conclusion was that supplementing the calcium binding capacity of vulnerable neurons may prevent cell damage.

Billman G E, McIlroy B, Johnson J D (1991),"Elevated myocardial calcium and its role in sudden cardiac death." FASEB J 5: 2586–2592 describes the treatment of cardiac arrhythmias with membrane permeant calcium chelators by the administration of a $Ca^{2+}$ buffer to dogs. The dogs were found to have a lesser chance of having a fatal electrical dysfunction of the heart. This article teaches that when membrane permeant calcium buffers are given to dogs, the electrical activity of their hearts is altered.

Niesen C, Charlton M P, Carlen P L (1991) "Postsynaptic and presynaptic effects of the calcium chelator BAPTA on synaptic transmission in rat hippocampal dentate granule neurons". Brain Res 555: 319–325, shows that the membrane-permeant $Ca^{2+}$ chelator BAPTA-AM can effect electrical activity of neurons when applied in vitro to an isolated brain slice preparation. The observed effects are similar to those seen when BAPTA salt is injected directly into neurons through a glass microelectrode. However, this article does not provide data to indicate that BAPTA-AM might be neuroprotective.

Carpenter-Deyo L, Duimstra J R, Hedstrom O, Reed D J (1991), "Toxicity to isolated hepatocytes caused by the intracellular calcium indicator, Quin 2". J Pharmacol Exp Therapeut 258: 739–746, teaches that membrane-permeant calcium buffers, (acetoxymethyl esters of Quin 2, Indo 1, Fluo 3, 5,5'-Dimethyl BAPTA) when applied to isolated liver cells, in vitro, cause toxicity to those cells. This article leads away from a teaching that membrane-permeant $Ca^{2+}$ buffers prevent toxicity in vivo.

K. G. Baimbridge and K. M. Abdel-Hamid, "Intraneuronal $Ca^{2+}$ buffering with BAPTA enhances glutamate excitotoxicity in vitro and ischemic damage in vivo, "Society for Neuroscience Abstracts, 18, 1992, .571.4, 22nd Annual Meeting, Anaheim, Calif., Oct. 25–30, 1992, teaches that when BAPTA-AM is given to cultured neurons in vitro, the toxicity of glutamate is greatly enhanced. Further, that when BAPTA-AM is injected directly into the rat brain in vivo prior to giving the rat a stroke, the damaging effects of the stroke are greatly enhanced. This article also leads away from a teaching that membrane permeant $Ca^{2+}$ buffers prevent in vivo toxicity.

REFERENCE LIST

The present specification refers to the following publications, each of which is expressly incorporated by reference herein.

PUBLICATIONS

1. Armitage P. Berry G (1987), "Statistical Methods in Medical Research." *Oxford: Blackwell Scientific Publications.*
2. Billman G E, McIlroy B, Johnson J D (1991), "Elevated myocardial calcium and its role in sudden cardiac death." *FASEB J.* 5: 2586–2592.
3. Brint S, Jacewicz M. Kiessling M, Tanabe J, Pulsinelli W (1988), "Focal brain ischemia in the rat: Methods for reproducible neocortical infarction using tandem occlusion of the distal middle cerebral and ipsilateral common carotid artery." *J. Cereb Blood Flow Metab* 8: 474–485.
4. Buchan A M, Xue D. Slivka A (1992), "A new model of temporary focal neocortical ischemia in the rat." *Stroke* 23: 273–279.
5. Carpenter-Deyo L, Duimstra J R, Hedstrom O, Reed J D (1991), "Toxicity to isolated hepatocytes caused by the intracellular calcium indicator, Quin 2." *J. Pharmacol Exp Therapeut* 258: 739–746.
6. Glaum S R, Scholz W K, Miller R J (1990), "Acute- and the long-term glutamate-mediated regulation of [Ca2+]i in rat hippocampal pyramidal neurons in vitro." *Journal of Pharmacology & Experimental Therapeutics,* 253: 1293–1302.
7. Goldman W F, Bova S, Blaustein M P (1990), "Measurement of intracellular $Ca^{2+}$ in cultured arterial smooth muscle cells using fura-2 and digital imaging microscopy." *Cell Calcium* 11: 221–231.
8. Grynkiewicz G. Poenie M, Tsien R Y (1985), "A new generation of calcium indicators with greatly improved fluorescence properties." *J. Biol. Chem* 260: 3440–3450.
9. Guthrie P B, Brenneman D E, Neale E A (1987), "Morphological and biochemical differences expressed in separate dissociated cell cultures of dorsal and ventral halves of the mouse spinal cord." *Brain Res* 420: 313–323.
10. Kudo Y, Takeda K, Yamazaki K (1990), "Quin2 protects neurons against cell death due to Ca2+ overload." *Brain Res* 528: 48–54.
11. Moore E D W, Becker P L, Fogarty K E, Williams D A, Fay F S (1990), "$Ca^{2+}$ imaging in single living cells: Theoretical and practical issues." *Cell Calcium* 11: 157–179.
12. Niesen C, Charlton M P, Carlen P L (1991), "Postsynaptic and presynaptic effects of the calcium chelator BAPTA on synaptic transmission in rat hippocampal dentate granule neurons." *Brain Res* 555: 319–325.
13. Park C K, Mendelow A D, Graham D I, McCullock J, Teasdale G M (1988), "Correlation of triphenyltetrazolium chloride perfusion staining with conventional neurohistology in the detection of early brain ischaemia." *Neuropathol Appl Neurobiol* 14: 289–298.
14. Randall R D, Thayer S A (1992), "Glutamate-induced calcium transient triggers delayed calcium overload and neurotoxicity in rat hippocampal neurons." *J. Neurosci* 12: 1882–1895.
15. Regan R F, Choi D W (1991), "Glutamate neurotoxicity in spinal cord cell culture." *Neuroscience* 43: 585–591.
16. Scharfman H E, Schwartzkroin P A (1989), "Protection of dentate hilar cells from prolonged stimulation by intracellular calcium chelation." *Science* 246: 257–260.
17. Tymianski M, Charlton M P, Carlen P L, Tator C H (1992), "Source specificity of early calcium neurotoxicity in cultured spinal neurons." *J. Neurosci* (Accepted with revisions Aug. 28, 1992).
18. Williams D A, Fay F S (1990), "Intracellular calibration of the fluorescent calcium indicator fura-2." *Cell Calcium* 11: 75–83.
19. K. G. Baimbridge and K. M. Abdel-Hamid, "Intraneuronal $Ca^{2+}$ buffering with BAPTA enhances glutamate excitotoxicity in vitro and ischemic damage in vivo, "Society for Neuroscience Abstracts, 18, 1992, 571.4, 22nd Annual Meeting, Anaheim, Calif., Oct. 25–30, 1992.
20. Tymianski, M. and Tator C. H., "A Novel Approach to Preventing $Ca^{2+}$ Neurotoxicity with Membrane-Permeant Calcium Chelators", The Canadian Journal of Neurological Sciences, #2, May 19, 1992.

PATENTS

1. U.S. Pat. No. 4,806,604, issued Feb. 21, 1989, to Tsien et al for "Photosensitive Calcium Chelators".
2. U.S. Pat. No. 5,049,673, issued Sep. 17, 1991, to Tsien et al for "Fluorescent Indicator Dyes for Calcium Working at Long Wavelengths".
3. U.S. Pat. No. 5,141,627 issued Aug. 25, 1992, to Tsian et al, for "Chelators whose Affinity for Calcium Ion is increased by Illumination."

As a result of extensive investigations, we have discovered a method of reducing the damaging effect of an injury to mammalian cells in vivo by the treatment of the cells with a cell membrane permeant calcium buffer.

SUMMARY OF THE INVENTION

It is an object of the present invention to provide in its broadest aspect a method of reducing the damaging effect of an injury to mammalian cells.

In a further object, the invention provides pharmaceutical compositions for use in treating mammals to reduce the damaging effect of an injury to mammalian tissue.

The present invention is based on the discovery of a neuroprotective effect against excitotoxic and ischemic injury by the manipulation of, intracellular $Ca^{2+}$ buffering capacity not requiring $Ca^{2+}$ influx blockade. This discovery is applicable to protection of all neuronal types and further addresses the possibility that in some cases, $Ca^{2+}$ neurotoxicity results from internal $Ca^{2+}$ release from intracellular storage sites.

Surprisingly, we have discovered that a number of membrane permeant $Ca^{2+}$ buffers prevent $Ca^{2+}$ mediated excitotoxicity in spinal neurons in vitro and significantly decrease neuronal death and infarction volume following cerebral ischemia in vivo.

Thus, in its broadest aspect the invention provides a method of controlling the concentration of $Ca^{2+}$ ions in the vicinity of ion channel pores of cells to prevent the diffusion of toxic amounts of said $Ca^{2+}$ ions to subcellular sites located near the source of $Ca^{2+}$ influx to prevent the triggering of neurotoxic phenomena, said method comprising administering an effective, non-toxic amount of a membrane permeant $Ca^{2+}$ buffer to said cell in vivo.

The invention further provides in one aspect a method of reducing the damaging effect of an injury to cells in mammalian tissue and treatment of epilepsy, said method comprising treating said tissue in vivo with a damage reducing, non-toxic, effective amount of a cell membrane permeant calcium buffer.

The buffer is, preferably, present in an amount to reduce or maintain intracellular calcium ion concentration to below millimolar levels.

Preferably, the cell membrane permeant buffer is a calcium ion chelating agent and more preferably a buffer having a $K_D$ selected from the range $1 \times 10^{-4}$ to $1 \times 10^{-8}$ Molar. Yet more preferably, the buffer is essentially calcium selective over other metal ions to provide minimal disruption to other metal e.g. Fe , Mg , K, Na, ion balances in the cell.

By the term $K_D$ is meant the ratio of the forward and reverse rate constants of the dissociation of the buffer -calcium salt (BCa) to buffer (B) and $Ca^{2+}$ ions as represented by the general equation $$BCa \underset{K_2}{\overset{K_1}{\rightleftharpoons}} B + Ca^{2+}; K_D = \frac{K_1}{K_2}$$

To effectively protect mammalian cells against injure, preferably, the effective amounts of $Ca^{2+}$ buffer inside the cell should be in the concentration range of 10 μM to 10 mM. This keeps intracellular calcium concentrations from rising to millimolar levels during injuries to mammalian cells in whole animals under conditions which are relevant for instituting therapy, i.e. clinically-relevant situations, such as, stroke, as opposed to clinically irrelevant situations, such as, being torn to bits by an atomic blast.

In a first form, the new compounds of use in the practice of the invention are comprised of a BAPTA-like chelator, in which the two halves of the chelator are linked by a linkage selected from the group comprised of: (a) a simple 1,2-ethanediyl ($-CH_2CH_2-$) moiety having bulky substituents such as $-CH_3$, $-C_2H_5$, or $-CH_2OH$ added thereto, (b) a 1,2-ethanediyl moiety incorporated into a carbocyclic ring and, (c) a 1,2-ethanedlyl moiety incorporated into a heterocyclic ring; wherein the chelator is coupled to a single 2-nitrobenzyl derivative, which in turn is a photochemical precursor of a 2-nitrosobenzophenone. In this form the new compounds are comprised of a chemical compound having the generic formula;

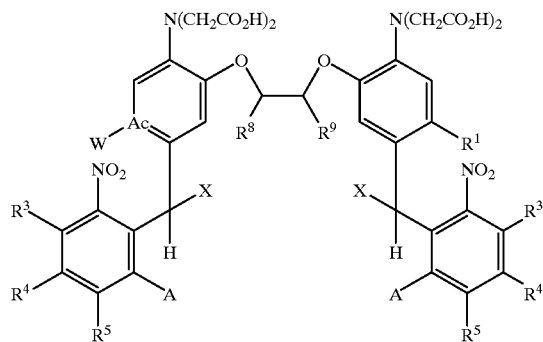

and the pharmaceutically acceptable nontoxic salts and esters thereof wherein:

A is $-NO_2$ or $-H$;
$R^1$ is selected from the group comprised of $-H$ (unless $R^2$ is also H), $-CH_3$, $-F$, $-Cl$, and $-Br$;
$R^2$ is selected from the group comprised of $-H$ (unless $R^1$ is also H), $-CH_3$, $-F$, $-Cl$, $-Br$, and $C_1-C_4$ alkoxy;
$R^3$, $R^4$ and $R^5$ are independently $-H$, OH, $NR^6R^7$, or alkoxy, or
$R^3$ and $R^4$ together are $-OCH_2O-$ or $-OCH_2CH_2O-$ and $R^5$ is $-H$, OH, $NR6R^7$, or alkoxy, or
$R^4$ and $R^5$ together are $-OCH_2O-$ or $OCH_2CH_2O-$ and $R^3$ is $-H$, OH, $NR^6R^7$, or alkoxy;
X is selected from the group comprised of $-OH$, alkoxy, $-Cl$, $Br$, $-NR^{67}$, $-OCOCH_3$, $-OCOCF_3$, $-OCOCH_2NH_2$, $-OPO_3H$, and $-OSO_2CH_3$;
$R^6$ and $R^7$ are independently $-H$, methyl or ethyl;
$R^8$ and $R^9$ are independently $-H$, $-CH_3$, $-C_2H_5$, or $-CH_2OH$ except that both may not be $-H$ simultaneously; or $R^8$ and $R^9$ together are $-(CH_2)_m-Y-(CH_2)_n-$ where m and n are independently 1 or 2 and Y is selected from the group comprised of $-CH_2-$, $-O-$, $-NR^6-$, $-S-$, and $-S-S-$; and
W is $-H$, $-OH$, or $-NHR^6$.

In a second form, the compounds are comprised of a BAPTA-like chelator, in which the two halves of the chelator are linked by a linkage selected from the group comprised of: (a) a simple 1,2-ethanediyl ($-CH_2CH_2-$) moiety having bulky substituents such as $-CH_3-$, $-C_2H_5$, or $-CH_2OH$ added thereto, (b) a 1,2-ethanediyl moiety incorporated into a carbocyclic ring and, (c) a 1,2-ethanediyl moiety incorporated into a heterocyclic ring; wherein the chelator is coupled to two 2-nitrobenzyl derivatives, themselves photochemical precursors of the related 2-nitrosobenzophenones. In this form, the compounds are comprised of a chemical compound having the generic formula:

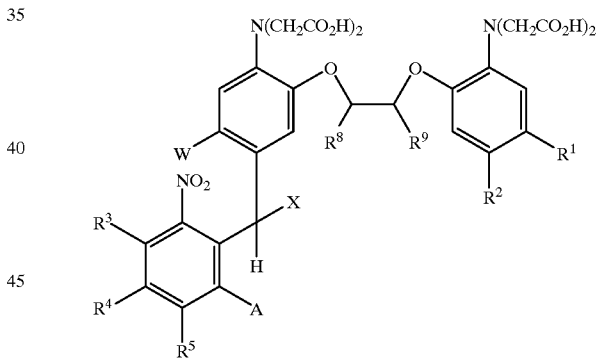

and the pharmaceutically acceptable non-toxic salts and esters thereof wherein:

A is $-NO_2$ or $-H$;
$R^3$, $R^4$ and $R^5$ are independently $-H$, OH, $NR^6R^7$, or alkoxy, or
$R^3$ and $R^4$ together are $-OCH_2O-$ or $-OCH_2CH_2O-$ and $R^5$ is $-H$, OH, $NR^6R^7$, or alkoxy, or
$R^4$ and $R^5$ together are $-OCH_2O-$ or $-OCH_2CH_2O-$ and $R^3$ is $-H$, OH, $NR6R^7$, or alkoxy;
X is selected from the group comprised of OH, alkoxy, $-Cl$, $-Br$, $-NRR7$, $-OCOCH_3$, $-OCOCF_3$, $-OCOCH_2NH_2$, $-OPO_3H$, and $-OSO_2CH_3$;
$R^6$ and $R^7$ are independently $-H$, methyl or ethyl;
$R^8$ and $R^9$ are independently $-H$ or $-CH_3$, or $-C_2H_5$ or $-CH_2OH$ except that both may not be $-H$ simultaneously;
or $R^8$ and $R^9$ together are $-(CH_2)_m-Y-(CH_2)_n-$ where m and n are independently 1 or 2 and Y is selected from the group comprised of —$CH_2$—, —O—, —$NR^6$—, —S—, and —S—S—; and W is —H, —OH, or —$NHR^6$.

In a third form, the compounds of use in the practise of the invention fall within the general formula:

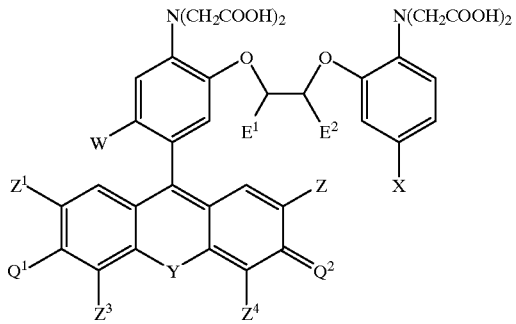

and the pharmaceutically acceptable non-toxic salts and esters thereof wherein:

$E^1$ and $E^2$ are independently H, $CH_3$ $C_2H_5$, $CH_2OH$, COOH, or $CH_2COOH$, or $E^1$ and $E^2$ together are —($CH_2$)m—V—($CH_2$)n— where m and n are independently 1 or 2 and V is selected from the group consisting of —$CH_2$—, —O—, NH—, —NMc—, —S—, and —S——S—;

W is H, OH, or COOH;

X is H, Me, COOH, F, Cl, Br, I or $NO_2$

Y is —O—, —NMe—, —S—, —$CH_2$—, —$CMe_2$—, —$CF_2$—, or a direct sigma bond making a five-membered central ring;

$Z^1, Z^2, Z^3$, and $Z^4$ are independently H, F, Cl, Br, I, or Me, and $Q^1, Q^2$ equal $R_1R_2N$—, or HO—, O=, where $R^1$ and $R_2$ are independently selected from the group consisting of H, Me, and Et;

or $Z^1, Q^1$, or $Z^3$ together are

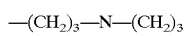

and

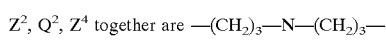

Preferably, the tetraacetic acid esters are alpha-acyloxyalkyl esters, and more preferably, the alpha-acyloxyalky esters are acetoxymethyl esters.

In a fourth form, the chemical compound has the general formula:

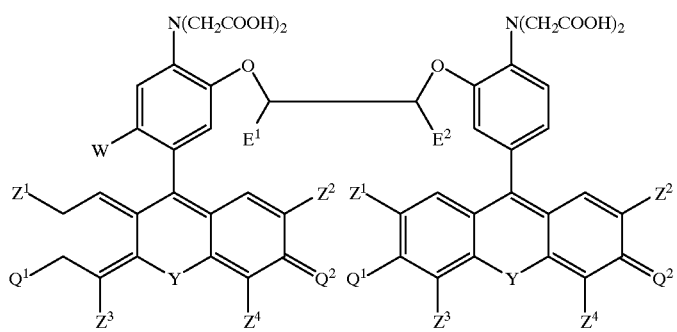

and the pharmaceutically acceptable non-toxic salts and esters thereof wherein:

$E^1$ and $E^2$ are independently H, $CH_3$, $C_2H_5$, $CH_2OH$, COOH, or $CH_2COOH$, or E1 and $E^2$ together are —($CH_2$)$_m$—V—($CH_2$)$_n$—where m and n are independently 1 or 2 and V is selected from the group consisting of $CH_2$—, —O—, —NH—, —NMe—, —S—, and —S—S—;

W is H, OH, or COOH;

X is H, Me, COOH, F, Cl, Br, I, or $NO_2$;

Y is —O—, —NMe—, —S—, —$CH_2$—, —$CMe_2$—, —$CF_2$—, —CO.— or a direct sigma bond making five-membered central ring;

$Z^1, Z^2, Z^3$, and $Z^4$ are independently H, F, Cl, Br, I, or Me, and $Q^1, Q^2$ equal $R_1R_2N$—,

or HO—, O= or $R_1R_2N$—, O—, where $R^1$ and $R_2$ are independently selected from the group consisting of H, Me, and Et; or $Z^1, Q^1, Z^3$ together are

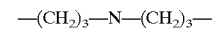

and $Z^2, Q^2, Z^4$ together are

In a fifth form, the chemical of use in the practise of the invention is a compound of the formula:

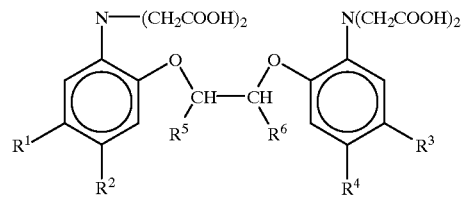

and the salts or the non-polymeric esters thereof wherein $R^1$ and $R^3$ are each independently selected from —H, OH, —$CH_3$, —F, Cl, —Br, —I, —COOH. —CN, —$NO_2$ or —$NHR^7$ wherein $R^7$, is independently selected from —H, methyl or ethyl;

$R^2$ is —(C=O)$CR^8$—N—N, wherein $R^8$ is independently selected from —H, C1–C4 alkyl, phenyl, —COOH, —$COOR^7$ —(C—O)$CH_3$, or —CF3 wherein $R_7$ is defined hereinabove;

$R^4$ is independently selected from $R^2$, —H, —$CH_3$, —$CH_2CH_3$, —F, —Cl—, —Br, —I, —COOH, —CN or —$NO_2$;

$R^5$ and $R^6$ are each independently selected from —H, —$CH_3$, —$C_2H_5$, phenyl, or —$CH_2OH$, or $R^5$ and $R^6$ together form —($CH_2$)$_m$—Y—($CH_2$)$_n$— where m and n are each independently 1 or 2, and Y is selected from —$CH_2$—, —O—, —$NHR^7$, —S— or —S—S—, wherein $R^7$ is defined hereinabove.

DEFINITIONS

In the present specification and claims, reference will be made to phrases and terms of art which are expressly defined for use herein as follows:

As used herein, "$[Ca^{2+}]i$" means intracellular free calcium.

As used herein, "EGTA" means ethylene glycol bis(-beta-aminoethyl ether-)-N,N,N',N'-tetraacetic acid.

As used herein, "BAPTA" means 1,2-bis(2-aminophenoxy)ethane N,N,N',N'-tetraacetic acid.

As used herein, "quin-2" means 2-[[2 -bis (carboxymethyl) amino]-5-methylphenoxy] -6-methoxy-8-bis(carobxymethyl)amino]quinolline.

As used herein, "BAPTA-like" means substituted derivatives of BAPTA which retain the essential characteristic of two bis (carboxymethyl) amino-substituted phenyl rings, said rings being linked at the positions ortho to the amines through a four atom bridge wherein the atom adjacent to each phenyl ring is N or O and the two center atoms are each C. By this definition, it is means that "BAPTA-like" includes compounds like quin-1 and quin-2.

As used herein, pharmaceutically acceptable esters mean those readily hydrolyzable esters which are known and used in the pharmaceutical industry, especially alpha-acyloxyalkyl esters.

As used herein pharmaceutically acceptable non-toxic salts mean carboxylic acid salts wherein the counterion or ions are all Na, K, $NR_4$=+ (where R=H, $C_1$–$C_4$ alkyl or a mixture thereof), choline, N-methyl-glucamine, Ca, or Mg, or some combination of these counterions, or some combination of acid salts or these counterions plus free acid groups.

By the term "cell membrane permeant calcium buffer" is meant a calcium ion chelating agent which per se is membrane permeant or a membrane permeant derivative thereof which releases said calcium ion chelating agent within the cell, for example ester, amide and other suitable derivatives which release the chelating agent per se, and pharmaceutically acceptable non-toxic salts thereof.

Examples of most preferred calcium buffers of use in the practise of the invention are those known in the art as follows:

BAPTA-AM (1,2 - bis (2-aminophenoxy) ethan - N,N,$N^1$, $N^1$-tetraacetic acid - acetoxymethyl ester;

EGTA-AM (ethyleneglycol bis 2-aminoethyl ether) N,N,$N^{1,}$ $N^1$-tetraacetic acid acetoxymethyl ester;

5,5'dibromo BAPTA-AM 5,5'- difluoro BAPTA-AM 4,4'-difluoro BAPTA-AM

The approximate dissociation constants for $Ca^{2+}$ of the above buffers are set out in following Table 1.

TABLE 1

| Chelator | Approximate $K_d$** | | |
|---|---|---|---|
| EGTA-AM | 100 nM | | |
| BAPTA-AM | 160 nM | in | 0 mM Mg |
| | 440 nM | in | 1 mM Mg |
| 5,5'-$Br_2$BAPTA-AM | 3600 nM | | |
| 5,5'-$F_2$BAPTA-AM | 660 nM | in | 0 mM Mg |
| | 706 nM | in | 1 mM Mg |
| 4,4'-$F_2$BAPTA-AM | 4600 nM | in | 0 mM Mg |

**Molecular Probes Inc. Eugene, Oregon.

The method of reducing the damaging effect of an injury to mammalian cells applies to the application of the cell membrane permeant calcium buffer by way of treatment after the injury has been sustained.

In an alternative method according to the invention the cell membrane permeant calcium buffer can be used as a prophylactic to reduce the extent of the injury to the cell by the application of the buffer prior to the injury being sustained.

The method of the present invention is applicable to injuries caused by a reduction in blood flow, oxygen flow nutrient flow, trauma, radiation, toxin exposure, infection, neoplasia or inflammation, to said tissue; and for the treatment of epilepsy.

Thus, treatment of a patient with a membrane permeant calcium buffer is performed under two major situations: 1) pre-treatment, when injury to the nervous system is anticipated, for example, as in upcoming surgery, and 2) post-treatment. The membrane permeant calcium buffer may be administered, for example, by one of the following four routes, namely, intravenously, intra-arterially, intrathecally, i.e. within the membranes surrounding the nervous tissue, or intraventricularly, i.e. directly into the chambers inside the brain. The buffer is, typically, administered in a suitable vehicle, in which the active ingredient buffer is either dissolved or suspended in a liquid and which permits the buffer to be delivered from the bloodstream into the nerve cells, thereby crossing the bloodbrain barrier without undue toxicity or from the cerebrospinal fluid into nerve cells without undue toxicity. Solutions would be, typically, alcohol solutions, dimethyl sulfoxide solutions, or aqueous solutions containing, for example, polyethylene glycol containing, for example, polyethylene glycol 400, Cremophor-EL or Cyclodextrin. Such vehicles are well-known in the art, and useful for the purpose of delivering a membrane permeant calcium chelator. Generally, in order for membrane permeant calcium buffers to work, they must be administered in a solvent that would prevent them from precipitating in the otherwise aqueous environment of the bloodstream. The solvent dimethylsulfoxide, DMSO, is one such useful solvent. Thus, treatment of a patient with a membrane permeant calcium buffer is performed.

Particular mammalian cells subjected to treatment according to the present invention are those of the nervous system, heart, liver, spleen, kidney, adrenal glands, gastrointestinal tract, vascular smooth muscle and the skin.

The cell membrane permeant calcium buffer may be administered to the mammal by methods well-known in the art, namely, intravenously, intra-arterially, topically, subcutaneously, by ingestion, intramuscular injection, inhalation, and the like. Preferably, for treatment of nerve cells, the most effective methods of administration are 1) intravenously; 2) intra-arterially, 3) intra-thecally and/or intra-cisternally; and 4) intra-ventricularly.

We have found that in the method according to the invention a sufficient period of time must be allowed for the cell membrane permeant calcium buffer to reach the damaged tissue and to enter the cells, and, if a derivative thereof, generate the buffer per se in vivo.

In a further aspect, the invention provides a cell membrane permeant calcium buffer for reducing the damaging effect of an injury to cells in mammalian tissue.

Preferably, the buffer is a chelating agent for the calcium ion, and more preferably, a buffer that is essentially calcium ion selective over other metal ions, such as for example, $Fe^{2+}$, $Mg^{2+}$, $K^+$ and $Na^+$. Calcium buffers having a $K_D$ selected from the range $1 \times 10^{-4}$ to $1 \times 10^{-8}$ Molar are most preferred.

Specific cell membrane permeant calcium buffers of value in the present invention are BAPTA-AM; EGTA-AM; 5,5'- difluoro BAPTA-AM and 4,4'- difluoro BAPTA-AM, azid 5,5'-dibromo BAPTA-AM, as hereinbefore defined.

In yet a further aspect, the invention provides pharmaceutic compositions for reducing the damaging effect of an injury to cells in mammalian tissue comprising a cell membrane permeant calcium buffer as hereinbefore defined in admixture with a suitable pharmaceutically acceptable diluent, carrier or adjuvant. It will be understood by the man skilled in the art that the pharmaceutically active cell membrane permeant calcium buffer should be present in pharmaceutically effective amounts.

DETAILED DESCRIPTION OF THE INVENTION

Methods for Experiments in Primary Neuronal Cultures

Tissue culture technique

Spinal neurons from E13 fetal Swiss mice were cultured for two weeks on glass coverslips coated with poly-D-lysine hydrobromide (M.W. 30,000–70,000, Sigma, P-7280). Dorsal root ganglia were excluded during the dissection. The neurons were as conventional dissociated primary neuronal cultures (*Guthrie* et al. 1987). All cultures were maintained in a humidified 5% —$CO_2$/95%—air atmosphere at 36.5° C., and were fed biweekly with a medium containing 58% minimal essential medium (MEM), 20% fetal bovine serum, and 20% distilled water, supplemented with (in mM) 40 glucose, 11.6 $NaHCO_3$, 0.4 L-glutamine and Insulin-Toronto, 80 biological units/100 ml of medium, balanced to 300 mOsm and pH 7.4 in 5% $CO_2$. At four days in vitro, the cultures were treated with 20µg/ml 5'-fluoro-deoxyuridine and 50µg/ml uridine for 24 hours to inhibit proliferation of non-neuronal cells. No antibiotics were employed. The presence of neurons and astrocytes in the cultures was confirmed by immunocytochemical staining for neurofilament, neuron-specific enolase, and glial fibrillary associated protein.

Loading of neurons with calcium indicator and $Ca^{2+}$ buffers

The cultures were incubated for 70 minutes in loading medium (78% MEM and 20% distilled water, supplemented to 40 mM D-Glucose, 1.0 mM $Mg^{2+}$, 20 mM HEPES, pH of 7.4 in 5% $CO_2$) containing 1µM fura-2-acetoxy-methyl ester (fura-2/AM; Molecular Probes Inc.) in a final concentration of 0.2% dimethyl sulfoxide (DMSO). After 10 min of loading with fura-2, the loading medium was supplemented with a membrane-permeant $Ca^{2+}$ buffer (Table 1 hereinafter) dissolved in the medium to its desired final concentration. The lipophilic membrane- permeant fura-2/AM penetrates into neurons and is converted by the action of intracellular esterases into a membrane-impermeant fura-2 salt, which is trapped intracellularly as a specific calcium indicator (Grynkiewicz et al. 1985). Non-fluorescent BAPTA and its derivatives permeate into neurons in the same manner (FIG. 2). After loading, the cultures were washed for 30 minutes in plain loading medium to attenuate any background fluorescence from residual extracellular calcium indicator.

Instrumentation

Cultures loaded with indicator were mounted in a microscope-stage incubator (Medical Systems Corp. model TC-202), and viewed with an inverted microscope (Nikon Diaphot-TMD equipped with Xenon epifluorescence optics) through a fluorite oil-immersion lens (Nikon CF UV-F ×40, NA=1.3) in contact with the coverslip bottom. A second-generation microchannel-plate intensified CCD-array camera (Quantex Corp. Model QX-100) recorded the 510nm fluorescence emissions from fura-2 in neurons excited through narrow band-pass filters (340±5,nm; 380±6.5nm; Omega Optical) housed in a computer-controlled filter wheel. All data were gathered on a 80386-based personal computer, and were archived on an optical disk drive (Panasonic, LF-5010). The system allowed for a time-resolution of 2 seconds between successive $[Ca^{2+}]_i$ measurements.

Calibration $[Ca^{2+}]_i$ was determined using in vitro-derived conversion factors used to generate a calibration curve described by the equation $[Ca^{2+}]_i = K_d(F_{min}/F_{max})[(R-R_{min})/(R_{max}-R)]$ in which $K_d$=224 nM, the dissociation constant for fura-2 (Grynkiewicz et al. 1985; for reviews see Moore et al. 1990; Goldman et al. 1990). To determine ($F_{min}/F_{max}$), $R_{min}$ and $R_{max}$, a glass-bottom slide with 100µL chambers containing control solution (see below), 1 µM fura-2 pentapotassium salt, and either a saturating calcium load (1 mM), or zero calcium with 10 mM EGTA was imaged. A third chamber containing control solution without fura-2 was used to generate background images. Typical values for conversion factors were: $F_{min}/F_{max}$=10.31, $R_{min}$=0.54, $R_{max}$=10.48. To generate ratio images, eight raw fluorescence images gathered at each wavelength (340 nm and 380 nm) were averaged, background subtracted, and converted on-line to calibrated fura-2 ratio images (340 nm/380 nm) using a pseudocolor display of $[Ca^{2+}]_i$. New background images were obtained for each experiment. The system was recalibrated following any adjustments to the apparatus. When plotting the time course of neuronal $[Ca^{2+}]_i$ (e.g., FIG. 1), if the measured $[Ca^{2+}]_i$ eventually rose to values exceeding those of the meaningful range of the calibration curve, the tracings were truncated for the purpose of clarity at values around 1500 nM $[Ca^{2+}]_i$ (asterisks). It was not possible to reproduce in the present neuronal preparation the in vivo calibrations described by others for non-neuronal cells (e.g., Williams and Fay, 1990), as spinal neurons exposed to varying concentrations of calcium ionophore (4-Bromo-A23187 at 0.5–10 µM) always underwent lysis prior to achieving $[Ca^{2+}]_i$ approaching those in the extracellular medium.

Drugs and solutions

The control solution contained in mM: 130 NaCl, 1.3 $CaCl_2$, 4.5 KCl, 22 D-glucose, 20 HEPES, 1.0 sodium pyruvate, and 0.001 glycine. All solutions were adjusted to 300 mOsm, pH of 7.4, and 36.5° C. prior to administration. EGTA/AM (Calbiochem) and all BAPTA-AM derivatives (Molecular probes inc.; see Table 1 and FIG. 2) were prepared as 30MM stocks in dry DMSO and dissolved to their final concentrations in the loading medium. During experiments, the final DMSO concentrations never exceeded 1.0%, a level which had no effect on $[ca^2+]_i$ or on neuronal survival in pilot studies.

Neuronal viability assays

Following each experiment, the cultures were incubated for 10 min at 36.5° C. with 2 µM ethidium homodimer and 1 µM calcein-AM. Ethidium homodimer binds to nuclear material in dead cells, whereas calcein-AM, by virtue of the enzymatic hydrolysis of the ester, is retained in living cells (Moore et al.1990). Thus, when excited in the fluorescein range (485–500 nm), dead cells appear red-orange, whereas living cells appear green. As a further measure of cell viability, the cultures were also superfused for 2 minutes with 0.4% trypan blue stain, and neuronal viability was confirmed with brightfield microscopy.

Experimental procedure

All experiments were performed at 36.5±5° C. Neurons loaded with fura-2 were superfused with control solution at 1–2 ml/min. $[Ca^{2+}]_i$ was measured simultaneously in several neurons in the field throughout the experiments. Baseline $[Ca^{2+}]_i$ was registered for 5–15 minutes, following which the neurons were exposed to a 50 min challenge with 250 μM glutamate (GLU). The rise in neuronal $[Ca^{2+}]_i$ was measured every 2 sec from the onset of the challenge until peak $[Ca^{2+}]_i$ was registered. Then, the frequency of $[Ca^{2+}]_i$ measurements was gradually reduced as $[Ca^{2+}]_i$ declined, reaching a measurement every 3 min when the decline in $[Ca^{2+}]_i$ ended. Following the 50 min challenge, neurons in some experiments were again superfused with control solution for a further 30 min.

Data Analysis

Statistical analyses were performed using ANOVA with post-hoc multiple comparisons using the Newman-Keuls procedure to determine significant differences between individual group means (see section 7.4 in Armitage and Berry, 1987). Linear and logistic regression analyses were employed to model and test probabilities of cell death. Where appropriate, survival analysis methods using the Kaplan-Meier survival model (see section 14.5 in Armitage and Berry, 1987) were employed to test time-dependent effects. Unless otherwise stated, mean values are provided with their standard errors (mean ±s.e.).

Methods for Experiments in Isolated Rat Brain Slices

Drugs and solutions

Calcium Crimson-AM, a fluorescent, membrane-permeant BAPTA-based $Ca^{2+}$ indicator (Molecular Probes Inc, C-3018), was dissolved in dry DMSO (400 mg in 0.5 ml DMSO) immediately prior to each experiment. Artificial cerebrospinal fluid (ACSF) contained in mM: NaCl 125, KCl 2.5, $NaH_2PO_4$ 1.25, $MgCl_2$ 2, $CaCl_2$ 2, $NaHCO_3$ 25 and glucose 10, with pH 7.4 aerated with 5% $CO_2$–95% $O_2$. The osmolarity of the ACSF was 300±5 m.osmol.

Experimental procedure

Fischer 344 rats weighing 240–300 grams were anaesthetized with 1.5% halothane (Fluothane, Ayerst Laboratories, Montreal) and nitrous oxide/oxygen 70%/30%, and maintained with positive pressure ventilation via a tracheostomy. Mean arterial pressure (MAP) measurements and venous access were obtained through polyethylene catheters inserted into the femoral artery and vein respectively. MAP was maintained at 80 mm Hg throughout the experiments. Core body temperature (measured with a rectal probe) and temporalis muscle temperature were monitored in each animal and maintained at 37±0.5° C. The protocol for loading rats with Calcium Crimson is shown in the inset of FIG. 7. Briefly, 400 mg of Calcium crimson-AM in 0.5 ml DMSO were then injected into the rat femoral vein over 60 min using an infusion pump. Control animals received 0.5 ml DMSO alone. Rats were always infused in pairs, with one animal serving as control. After a further 3 hours, the rats were decapitated, and transverse brain slices (400 μm) were obtained and maintained in ACSF at room temperature until used.

A rat brain slice loaded with Calcium Crimson was placed alongside a control slice in a glass-bottomed chamber. They were viewed at room temperature with a laser-scanning confocal microscope (Bio-Rad MRC 600) through a fluorite lens (Nikon CF UV-Fx10). In each experiment, both slices (control and loaded) were viewed with the same confocal settings, using a Rhodamine filter cube.

Methods for Experiments in Vivo a) Surgical Preparation

Forty-one male Fischer 344 rats (weight 275–340 grams) were anaesthetized with 2% Halothane and a mixture of nitrous oxide/oxygen (1:1) in a bell chamber. A tracheostomy was performed and mechanical ventilation initiated (Harvard rodent ventilator, Model 683). Maintenance anaesthesia was 1% Halothane titrated to blood pressure. Polyethylene tubing was inserted into the femoral artery and vein for continuous blood pressure monitoring and for drug and fluid administration. The ventilation was altered according to the arterial blood gases taken at regular intervals. Temperature was monitored with a rectal probe as well as a micro-probe placed in the temporalis muscle, and an overhead lamp was used to maintain the recorded rectal temperature at 37 degrees celsius. Vascular catheters were filled with heparinized saline (100 IU/ml).

b) Experimental Design

Two independent, blinded experiments were carried out. After the surgical preparation was complete and the blood gases had stabilized, the animal would be randomly allocated to an experimental group and begin an infusion (Harvard Infusion pump, Models 901,903) with a volume of 0.5 cc over a time period of 60 minutes. The cerebral ischemia was started 4 hours after the beginning of the infusion.

i) Study I:

Animals were randomized into two groups, one receiving an infusion of DMSO and the second receiving BAPTA/AM (18 mg/kg) in an identical solution of DMSO.

ii) Study II

There were five experimental groups in the second study, carried out by a different surgeon than the first study. Random allocation of animals was performed into the following infusion regimes:

1. saline
2. DMSO
3. BAPTA/AM in DMS0
4. 4,4'diflouro BAPTA in DMSO
5. 5,5'diflouro BAPTA in DMSO c) Cerebral Ischemia Thirty minutes prior to the completion of the 4 hour pre-treatment period, the surgical preparation for middle cerebral occlusion was started. The procedure used in both studies has been previously described (Brint et al 1988, Buchan et al 1992). Briefly, the left common carotid was exposed through the tracheostomy incision and the distal left middle cerebral artery was exposed via a small temporal craniectomy. As the pre-treatment period concluded, the common carotid was occluded with an aneurysm clip and the middle cerebral artery was cauterized and cut with the assistance of the operating microscope. The incisions were closed with sutures.

The post-ischemic period lasted 4 hours during which mean arterial blood pressure and arterial blood gases were monitored continuously. Core (rectal) and temporalis muscle temperature was maintained at 37±0.5 degrees celsius.

d) Outcome Methods

After completion of the 4 hour post-ischemic time period, an infusion with Triphenyltetrazolium chloride (TTC) and formaldehyde was performed as previously described (Park et al 1988). Briefly, the ascending aorta was cannulated through an abdominal incision and heparinized saline was infused until the effluent via a hole in the inferior vena cava was clear. Infusions of TTC followed by formaldehyde at a perfusion pressure of 80 mmHg concluded the perfusion fixation. The heads were removed and placed in formaldehyde for 24 hours before the brains were removed.

The brains were sectioned in eight coronal planes and evaluated for TTC staining. Two individuals, blinded to the experimental groups, recorded the TTC defect. The infarction volume was calculated on an image analysis system (MCID, Imaging Research Inc.) from the cross-sectional area of TTC defect in the eight coronal planes. The coronal brain slices were embedded in paraffin, cut by microtome into 7 micron sections and stained with hematoxylin and eosin. The histology was reviewed by two individuals, again blinded to the experimental group, and the infarction area demarcated on each of the eight coronal sections. The volume of infarction and the percent of cortex infarcted were calculated using the image analysis system.

Statistical analysis involved a comparison of the infarction volume or percent cortical infarction between treatment groups by Student T-Test for Study I and an analysis of variance with post hoc T-Tests for Study II. Correlation coefficients were calculated for TTC versus histological evaluation of infarction volume and the variability between individuals assessing the infarction.

BRIEF DESCRIPTION OF THE DRAWINGS

FIG. 2 represents the chemical structures of BAPTA-AM and related derivatives, and schemes outlining the de-esterification processes of BAPTA-AM and derivatives.

FIGS. 3A to 3F represent graphs giving the effects of membrane-permeant $Ca^{2+}$ buffers on $[Ca^{2+}]_i$ and secondary $Ca^{2+}$ overload. Individual tracings show the time-course of $[Ca^{2+}]_i$ in single neurons challenged with 250 μM glutamate (GLU; black bar). A. Stability of baseline $[Ca^{2+}]_i$ in the absence of GLU. B. In the absence of exogenous $[Ca^{2+}]$ buffers, GLU evokes a large primary $[Ca^{2+}]_i$ transient (arrow) which recovers to a lower "plateau", followed by secondary $[Ca^{2+}]$ overload (asterisks) in 12/15 neurons. C-F. Time course of $(Ca^{2+})_i$ in neurons pre-treated with BAPTA-AM (D,D), EGTA-AM (E), and 4,4'$F_2$-BAPTA-AM(F). At sufficient concentrations, BAPTA and EGTA ($K_d$=100 nM) attenuated the peak $[Ca^{2+}]_i$ rise, and protected neurons against secondary $Ca^{2+}$ overload (D,E). 4,4'$F_2$-BAPTA, a low affinity $Ca^{2+}$ buffer ($K_d$=2600 nM) was toxic to spinal neurons (F).

PART 1: Cell Culture Experiments

The application of exogenous glutamate to cultured CNS neurons is a commonly employed, and accepted model of neurotoxicity in vitro, and approximates the excitotoxic phenomena occurring in the CNS in vivo. Accordingly, a glutamate challenge was used as the cytotoxic stimulus in the present experiments. Using the digital imaging approach, $[Ca^{2+}]_i$ was measured simultaneously in several neurons (mean: 10 neurons per experiment, range 4–27). A total of 667 spinal neurons in 68 experiments were studied. Twenty three neurons (3.44%) were excluded from study because of consistently elevated $[Ca^{2+}]_i$ (>250 nM) during baseline measurements, leaving 644 neurons for statistical analyses of physiological parameters. All neurons were cultured for 14–17 days to ensure a uniform, high susceptibility to glutamate neurotoxicity between cultures (Regan and Choi, 1991). At this stage in vitro, the neurons exhibited extensive neurite formation, and were easily distinguished from surrounding cells by the presence of oval, phase-bright somata and by the morphology of their processes. The somal diameters of neurons used in these studies averaged 17±5.7 μm (mean±std. dev.). All related experiments were routinely performed in sister cultures, and the results were replicated in cultures from later dissections.

"$Ca^{2+}$ deregulation" is an early indicator of neuronal death.

Figure 1:
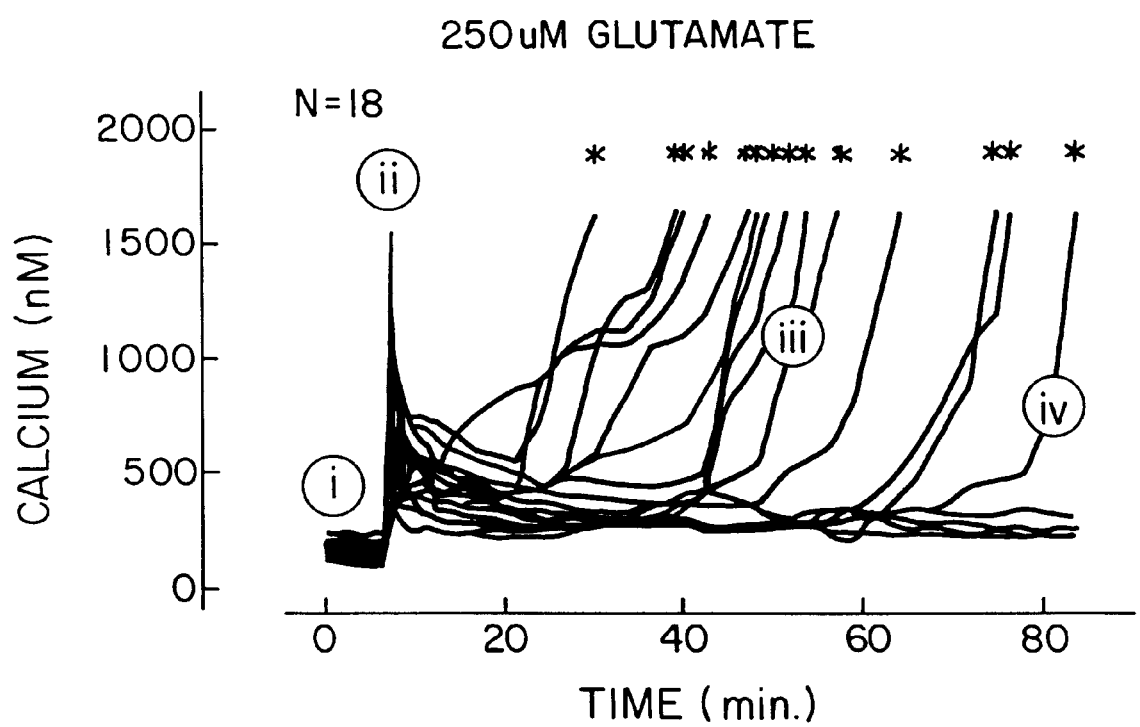
FIG. 1 represents a graph of time course of changes in intracellular calcium during neurotoxin L-glutamate-sodium application.

FIG. 1 shows that when spinal neurons were exposed to a 50 min challenge with 250 μM glutamate (GLU), $[Ca^{2+}]_i$ rose rapidly, and then decayed to a lower "plateau". Following termination of the challenge, $[Ca^{2+}]_i$ in surviving neurons remained at the new plateau, or returned toward basal levels. However, many neurons underwent a delayed, sustained, and generally irreversible rise in $[Ca^{2+}]_i$ which often exceeded the dynamic range of the $Ca^{2+}$ indicator (asterisks in FIG. 1A). This phenomenon closely paralleled neuronal staining with the vital dye trypan blue, indicating that it must have preceded- or coincided with- neuronal death. Observations in spinal neurons are in agreement with the recently reported observation that glutamate-induced $[Ca^{2+}]_i$ transients can trigger delayed $Ca^{2+}$ overload and neurotoxicity in hippocampal neurons following single (Randall and Thayer, 1992) or repeated (Glaum et al.1990) challenges. This "$Ca^{2+}$ deregulation" phenomenon, following its onset could not be arrested by blockade of $ca^{2+}$ channels by dihydropyridine (DHP) nimodipine (1 $\mu$M), nor by NMDA receptor blockade with DL-2-amino-5-phosphonovaleric acid (APV; 50 $\mu$M). Also, it was not immediately reversible in many neurons by switching to a zero-$Ca^{2+}$ buffer, indicating that this second rise in $[Ca^{2+}]_i$ did not result from non-specific plasma membrane leakiness, but more likely from a decompensation of cellular $Ca^{2+}$ homeostatic mechanisms. The process of $Ca^{2+}$ deregulation usually preceded positive staining with trypan blue or with ethidium homodimer, and lasted for up to 30–40 minutes before membrane lysis as judged by the loss of intracellular fura-2 fluorescence. While not bound by theory, this observation supports further the notion that secondary $Ca^{2+}$ overload precedes severe damage to the neuronal membrane.

Membrane-permeant $Ca^{2+}$ buffers prevent $Ca^{2+}$ deregulation and neuronal death in vitro.

We have found that the degree of toxicity triggered by $Ca^{2+}$ influx into neurons depends not only on a rise in $[Ca^{2+}]_i$, but also on the type of $Ca^{2+}$ influx pathway. In spinal neurons, $Ca^{2+}$ influx through NMDA receptor operated channels was considerably more damaging than the same degree of $Ca^{2+}$ rise triggered through other pathways (Tymianski et al. 1992). This is indicative that neurotoxicity is more pronounced when $Ca^{2+}$ enters neurons through NMDA receptor channels because they are preferentially co-localized with those processes which, when activated in an uncontrolled or excessive manner, lead to the expression of neurotoxicity. This was confirmed using a method for modulating glutamate-induced transmembrane $Ca^{2+}$ gradients independently of NMDA channels. This was achieved by loading neurons with membrane-permeant forms of various calcium buffers. These agents chelate $Ca^{2+}$ once it enters the neuron, but have no reported effects on NMDA channels. If initiation sites for neurotoxic cascades are truly localized in close physical proximity to NMDA channels, then fast $Ca^{2+}$-buffers with high cytomplasmic mobility (eg. BAPTA, $K_d$ Ca. 160 nM, $D_{BAPTA}$ approx. $2 \times 10^{-6}$ cm$^2$/sec) should prove neuroprotective by capturing $Ca^{2+}$ ions as they permeate through NMDA channels before they diffuse to their neurotoxicity "trigger sites" ($D_{Ca}$ approx. $0.2 \times 10^{-9}$ cm$^2$/sec). By the same token, a calcium buffer with similar $Ca^{2+}$ affinity but slower buffering kinetics (eg: EGTA, Kd also Ca. 100 nM at pH 7.2) might be less neuroprotective if it captured $Ca^{2+}$ too slowly, allowing it sufficient time to reach its neurotoxic site of action.

Spinal neurons in dissociated cultures were simultaneously loaded with fura 2-AM and with a $Ca^{2+}$ chelator (Table 1). They were then exposed to 50 min challenges with 250 $\mu$M glutamate as described previously. To ensure that loading with BAPTA-AM and EGTA-AM produced equivalent concentrations of the two $Ca^{2+}$ buffers in neurons, the buffers were present at 100 $\mu$M concentrations in the loading medium (approaching saturating concentrations for BAPTA-AM). The assumption was made that in the presence of excess membrane-permeant $Ca^{2+}$ buffer, the limiting factor in buffer loading would become the intracellular esterase activity, which presumably, would be equal in neurons from different experiments.

Figure 3F:
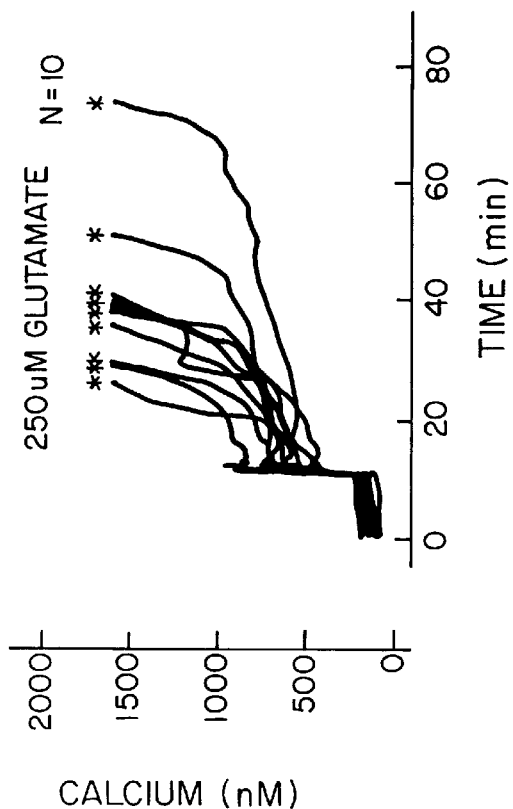
Figure 3E:
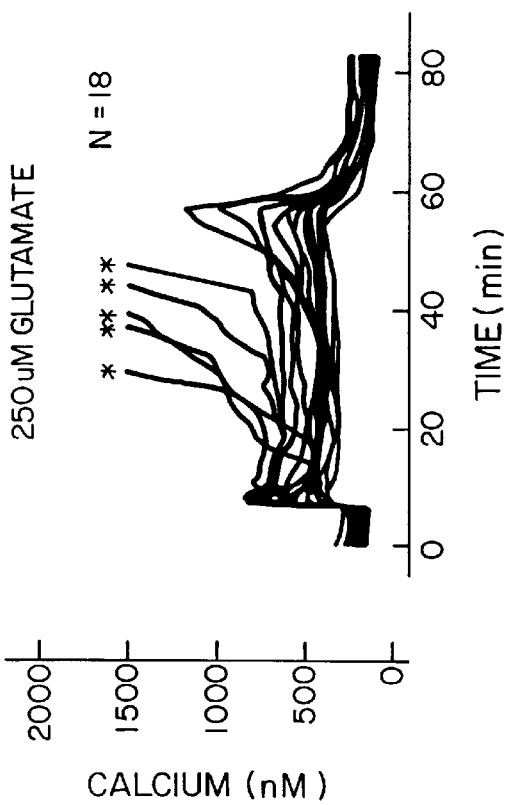

FIG. 3 illustrates representative experiments, showing that when neurons were pre-treated with 10 $\mu$M BAPTA-AM (FIG. 3C), the $[Ca^{2+}]_i$ transient amplitude was not attenuated as compared with controls (see FIG. 3B). However, the frequency of $Ca^{2+}$ deregulation (asterisks) was markedly decreased. Pretreatment of neurons with 100 $\mu$M BAPTA-AM (FIG. 3D), and 100 $\mu$M EGTA-AM (FIG. 3E) caused the glutamate-evoked $[Ca^{2+}]_i$ transient to be significantly attenuated. This effect was also accompanied by a decreased proportion of $Ca^{2+}$ deregulations as compared with controls. By contrast, neurons which were pretreated with 30 $\mu$M of 4,4'-F$_2$BAPTA, a buffer with a low $Ca^{2+}$ affinity ($K_d$ approx. 4600 nM), all succumbed to the 50 min glutamate challenge (FIG. 3F). FIG. 3A shows stability of the recordings throughout the time-period of the experiment.

Figure 4A:
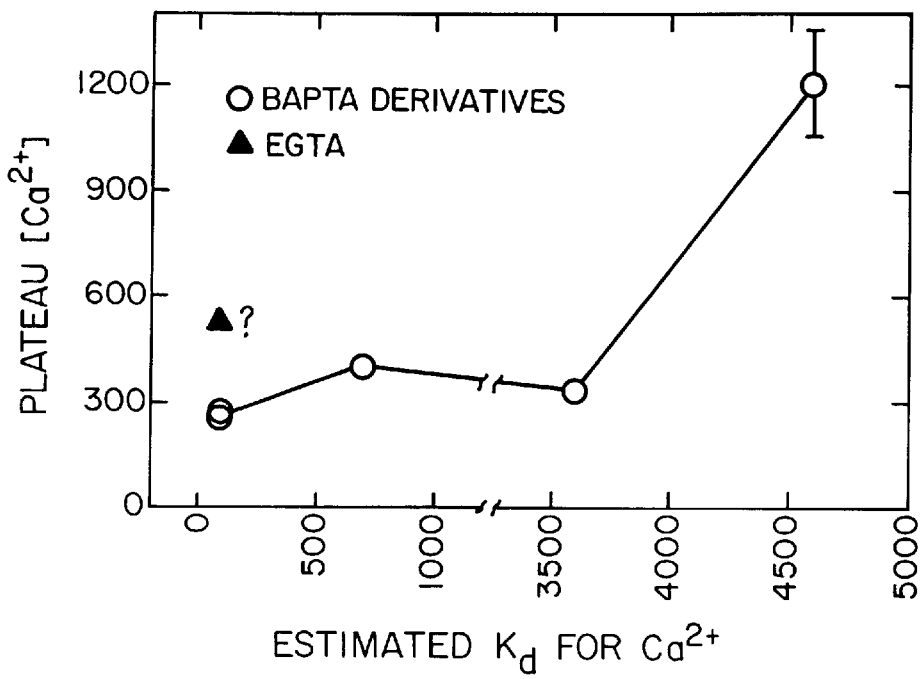
FIGS. 4A–4D represent graphs showing the relationships between $Ca^{2+}$ buffers, $[Ca^{2+}]_i$, $Ca^{2+}]_i$-affinity ($K_d$), and neuronal survival following glutamate challenge. Neurons were superfused with 250 μM glutamate as in FIG. 3. Symbols in A–C show mean values for all neurons treated with a given $Ca^{2+}$ buffer (total 450 neurons.) Standard errors are shown where they exceed the symbol size. A. Relationship between K and the fraction of dead neurons following recovery from the initial $[Ca^{2+}]_i$ transient (Plateau $[Ca^{2+}]_i$). B. Relationship between $K_d$ and the fraction of dead neurons in each $Ca^{2+}$ buffer group. C. Dominance of intracellular $Ca^{2+}$ buffering by exogenous buffers, illustrated by the linear relationship between the fraction of dead neurons and plateau $[Ca^{2+}]_i$ in neurons loaded with $Ca^{2+}$ buffers (Correlation Coefficient =0.986, p 0.0003). Note that control neurons (square) do not fall on this line. D. Effects of various $Ca^{2+}$ buffers on neuronal survival as gauged by trypan blue and by secondary $Ca^{2+}$ overload. Bars with different symbols are statistically different at p 0.001.
Figure 4B:
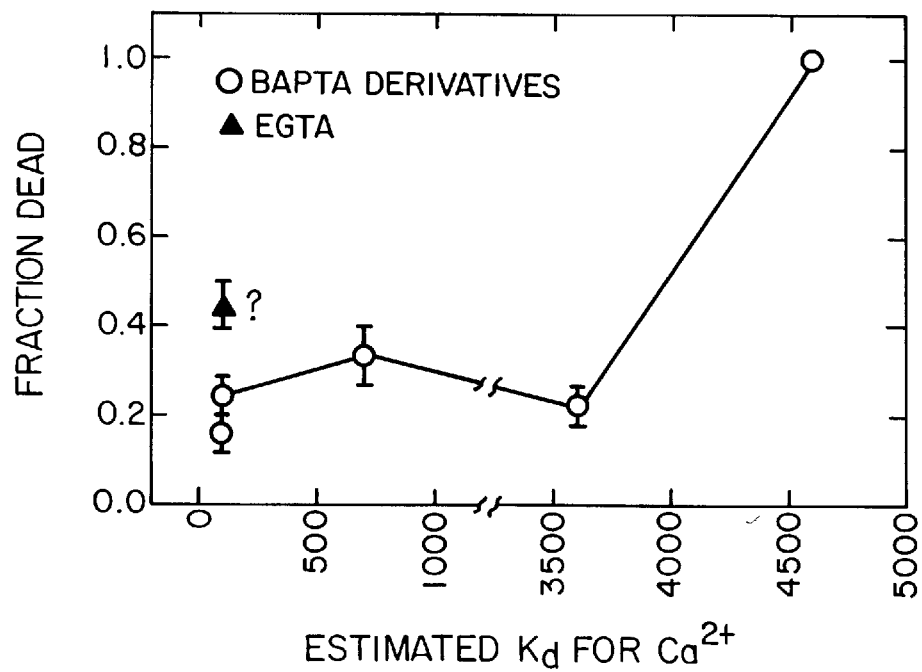
Figure 4C:
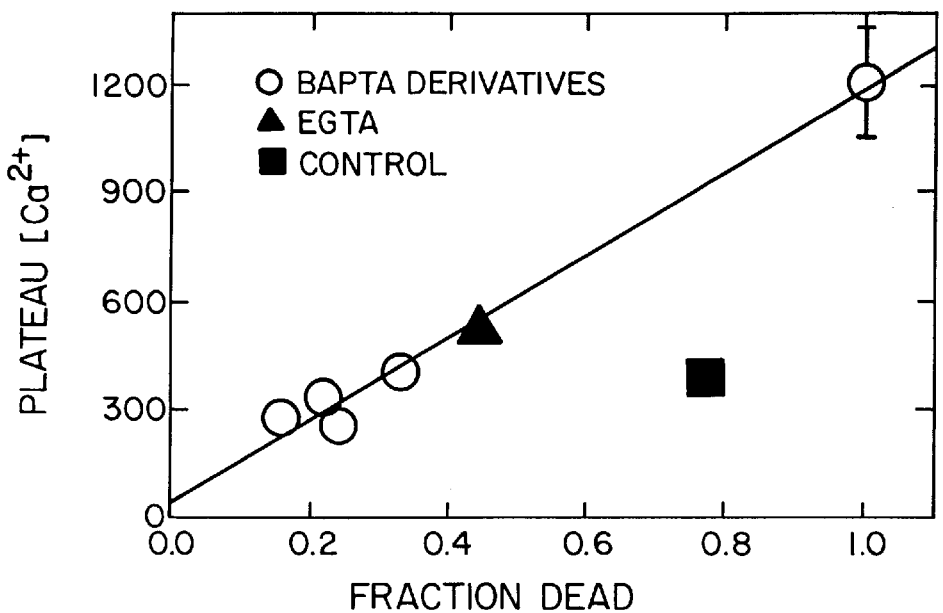
Figure 4D:
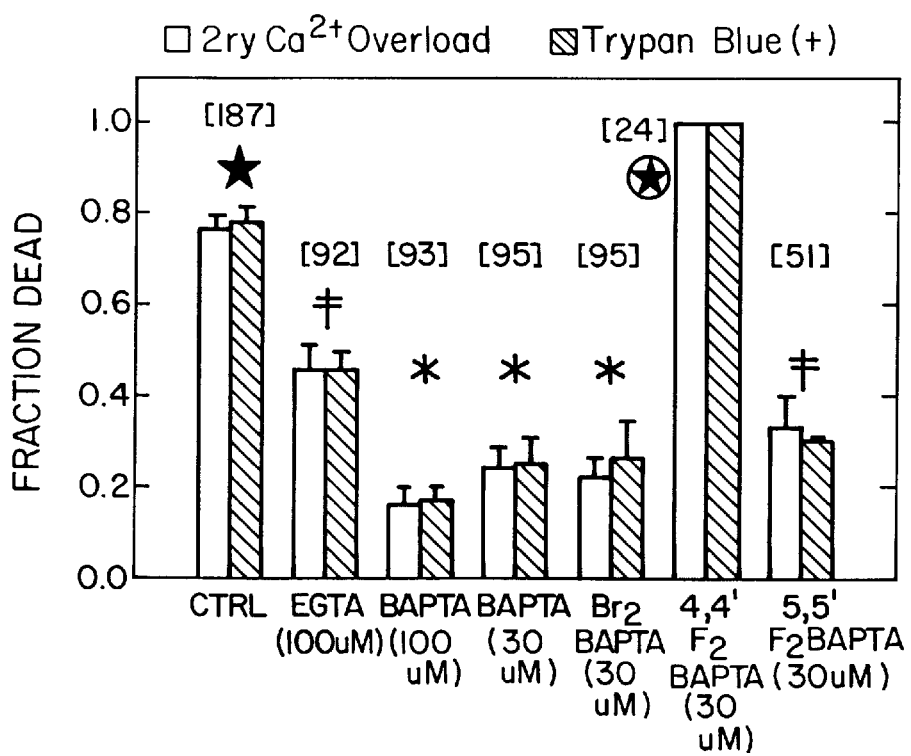
Figure 5:
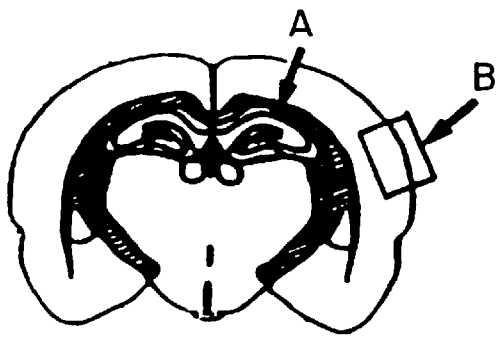
FIG. 5 represents the brain regions from which images were taken as shown by the arrows A and B.

FIG. 4D shows the survival outcomes for all spinal neurons challenged with 250 $\mu$M glutamate for 50 min. This challenge caused $Ca^{2+}$ deregulation and cell death in about 80% of neurons under control conditions (FIG. 4D, CTRL). The data show that all $Ca^{2+}$ buffers used in this study with the exception of 4,4'-F$_2$BAPTA-AM ($K_d$=4600 nM) were effective in reducing cell death. Particularly, when loaded into neurons at equivalent concentrations (100 $\mu$M), BAPTA the fast $Ca^{2+}$ buffer was considerably more neuroprotective than EGTA, the slower $Ca^{2+}$ buffer which has similar $Ca^{2+}$ affinity to BAPTA. This result supports our original hypothesis that $Ca^{2+}$ must diffuse relatively short distances within the cytoplasm to reach its neurotoxic site of action. The results also demonstrate that $[Ca^{2+}]_i$ must rise to micromolar concentrations in order to trigger neurotoxicity, because buffers with $K_d$'s of up to 3600 nM (Br$_2$BAPTA) were highly neuroprotective. The data indicate that $Ca^{2+}$ becomes neurotoxic when its concentration rises to levels approximating the $Ca^{2+}$ affinity of 4,4'-F$_2$BAPTA.

Among neurons loaded with $Ca^{2+}$ buffers, there was a linear relationship between the fraction of dead neurons in each experiment and the value of the $[Ca^{2+}]_i$ plateau reached when the initial $[Ca^{2+}]_i$ transient decayed to a steady-state level (FIG. 4C, R=0.986, p=0.0003). Plateau $[Ca^{2+}]_i$ values in control neurons (not loaded with $Ca^{2+}$ buffer) did not fall on the best-fit streight line in this relationship (solid square, FIG. 4C). This result in control neurons is consistent with data we have reported previously (Tymianski et al. 1992), which showed that cytoplasmic $Ca^{2+}$ indices (peak $[Ca^{2+}]_i$, average $[Ca^{2+}]_i$, and the area under the $[Ca^{2+}]_i$ time-course curve) did not correlate with neuronal mortality. The fact that plateau $[Ca^{2+}]_i$ correlated highly with cell death in buffer-loaded neurons in this study shows that the exogenously administered $Ca^{2+}$ buffers dominated over other cellular $Ca^{2+}$ homeostatic processes. Thus, the probability of cell death becomes a function of $[Ca^{2+}]_i$, rather than that of other cellular homeostatic processes.

FIG. 4A shows that plateau $[Ca^{2+}]_i$ in neurons loaded with BAPTA and its derivatives was clamped at a level logarithmically proportional to the buffer's $Ca^{2+}$ affinity. There was a similar relationship between the fraction of dead neurons in each experiment, and the buffer's $Ca^{2+}$ affinity (FIG. 4B). These relationships did not hold in the case of EGTA. A possible explanation for this is the latter buffer's slow buffering speed as compared with that of the BAPTA derivatives. Another possibility is that as intracellular pH decreases during cell death, the affinity of EGTA for $Ca^{2+}$ decreases, as this buffer is highly pH sensitive.

PART 2: Brain Slice Experiments

The above experiments show that exogenously applied $Ca^{2+}$ buffers are neuroprotective against glutamate-induced neuronal death. The following experiments were performed to show that these agents are successfully delivered into neurons in vivo (see above for methods). Adult Fischer 344 rats were anaesthetized with 1.5% halothane and 70%/30% Nitrous/$CO_2$. Calcium crimson-AM, a BAPTA derivative with an excitation maximum at 590 nm, was dissolved in DMSO and injected intravenously by infusion pump. Control animals received DMSO alone. Following this, the rats were decapitated, and transverse brain slices (400 µm) were obtained and viewed with a laser-scanning confocal microscope (Bio-Rad MRC 600). Control and loaded slices were viewed with the same confocal settings. The control confocal image of the hippocampal CA1 region showed mild autofluorescence from individual neuronal somata. The image from the hippocampal CA1 region in a rat loaded with Calcium Crimson-AM showed a bright flurescence in individual CA1 neurons.

Confocal microscopy images taken from rat brain slices show that Calcium Crimson-AM, a fluorescent derivative of BAPTA, could be delivered via intravenous infusion (see FIG. 3A) into neurons in the hippocampal CA1 region, and into cortical neurons. To ensure its solubility in rat blood and in extracellular fluid, Calcium Crimson-AM was dissolved in DMSO (400 µg in 0.5 ml). In control brain slices (DMSO alone), there was little or no visible fluorescence. By contrast, the fluorescence of Calcium Crimson was clearly visible in individual cortical and hippocampal CA1 neurons in slices taken from rats loaded with this $Ca^{2+}$ buffer. This showed the loading of membrane-permeant $Ca^{2+}$ buffers into individual CNS neurons via intravenous infusion.

PART 3: Experiments in Vivo

Figure 6:
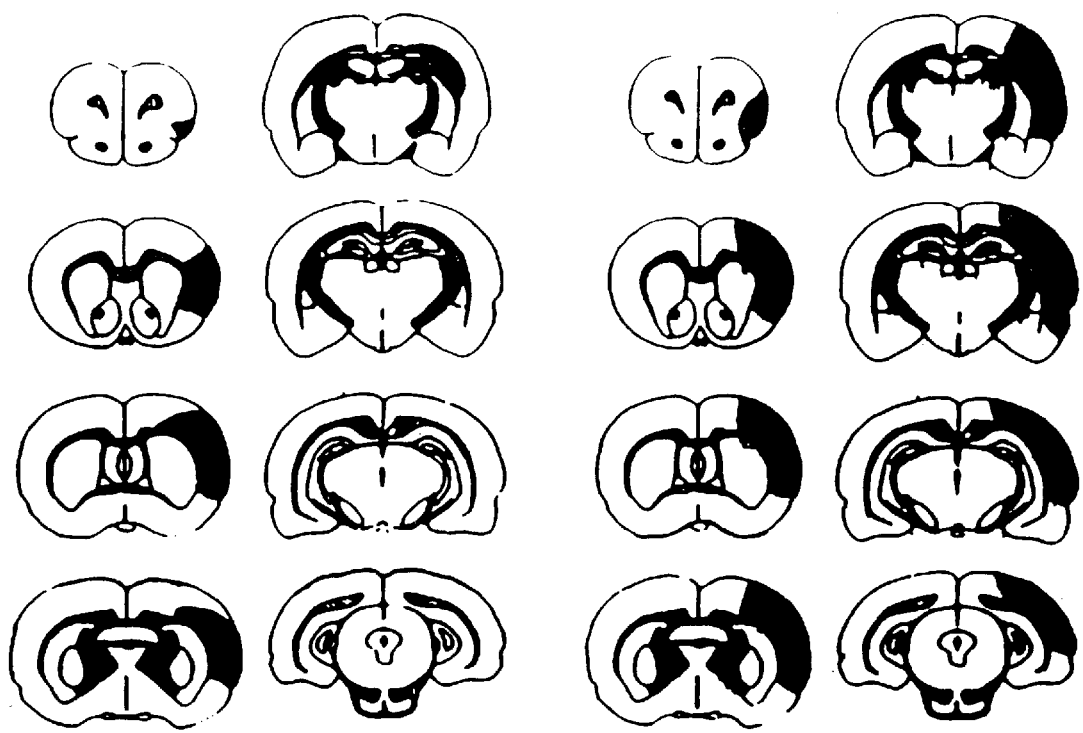
FIG. 6 shows the representative effects of BAPTA-AM on cortical infarction volume as determined by TTC method (MCA & CCA occlusion). Rats treated with BAPTA-AM or its derivatives (Rat no. 4) sustained significantly smaller cortical infarctions than controls (rat no. 6) after distal middle cerebral and ipsilateral common carotid occlusion. Infarction volumes in every case were computed from infarction area measurements performed on eight standardized coronal brain slices as shown here. The same templates were utilized for infarction volume assessment by triphenyltetrazolium chloride perfusion (TTC), and by standard histological means. Left hand diagram represents BAPTA-AM, 18 mg/Kg, delivered in 0.5 ml DMSO to rat no. 4; and right hand diagram represents control, 0.5 ml DMSO, with rat no. 6.
Figure 7A:
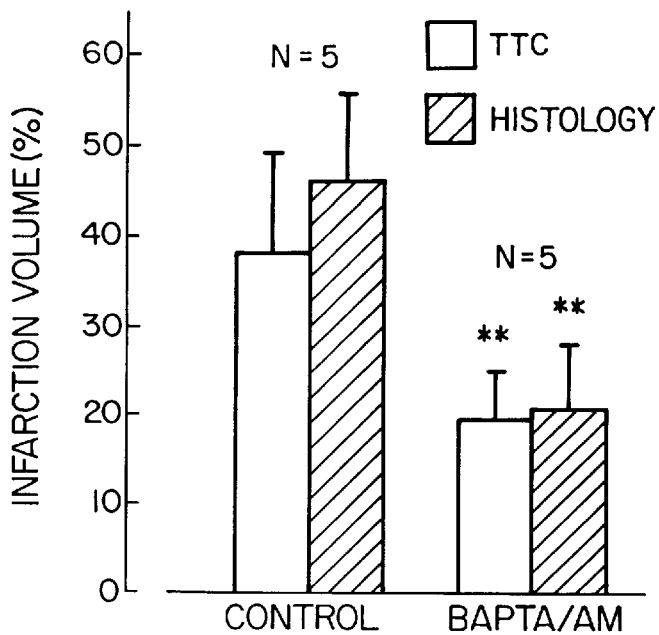
FIGS. 7A and 7B represent graphs showing that BAPTA-AM reduces the volume of infarction following focal cerebral ischemia. A. in a randomized, double blinded, placebo controlled trial, pretreatment with BAPTA-AM or its derivatives reduced focal infarction volume by 50% as compared with controls. Infarct volumes were assessed by two methods. First, by triphenyltetrazolium chloride (TTC) perfusion, a technique which delineates the infarction area by vitally staining non-infarcted tissues red, and second, by histological assessment of the infarction area. Infarction volumes were calculated as shown in FIG. 6. Results are shown as means ± standard deviations. B. Relationship between infarct volume assessment with TTC and histology.
Figure 7B:
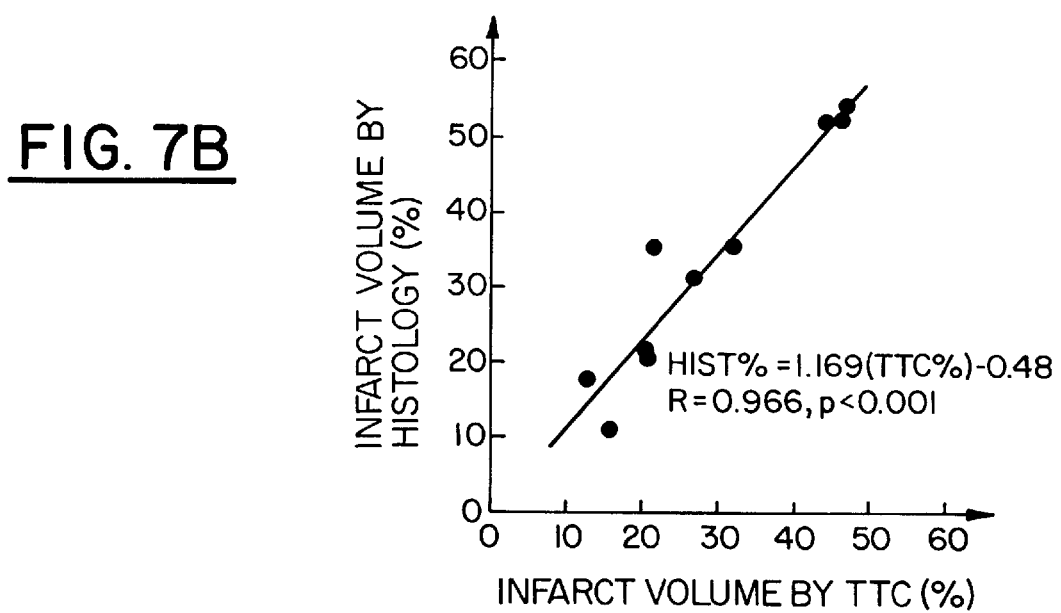
Figure 7C:
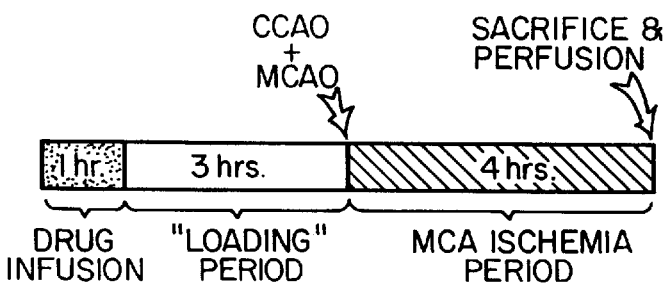
FIG. 7C illustrates the surgical protocol for both double-blinded randomized trials.

The above results show that membrane-permeant $Ca^{2+}$ buffers were neuroprotective in spinal neurons in vitro, and that they could be successfully delivered into the mammalian CNS. We have further shown that intracellular $Ca^{2+}$ chelation using exogenously-administered $Ca^{2+}$ buffers is as a useful neuroprotective strategy in vivo. FIG. 6 shows representative results from experiments in a first study, in which the neuroprotective effects of BAPTA-AM (18 mg/kg delivered in 0.5 ml DMSO) were evaluated in a rat cortical stroke model. The FIG. 6 shows that cortical stroke volumes were markedly attenuated in rats treated with BAPTA-AM (shaded areas in FIG. 6 left panel) as compared with controls (FIG. 6 right panel). Cortical infarction volumes were evaluated using two independent techniques: TTC and histology (see methods section above). FIG. 7B shows that both methods were reliable for assessing cortical infarction volume. The outcome of the first in vivo study is shown in FIG. 7A: There was a marked reduction in cortical stroke volume in rats treated with BAPTA-AM, as compared with controls. Control rats sustained stroke volumes of 38.32%±10.95% and 46.14%±9.52% (mean±standard deviation) using the TTC and histological assessments respectively. By contrast, rats pre-treated with BAPTA-AM sustained stroke volumes of 19.58%±5.41% and 20.62%±7.42% using the TTC and histology assessments respectively. Thus, the pretreatment of animals with BAPTA-AM accomplished a 50% reduction in cortical stroke volume (p=0.008 and 0.001 for TTC and histology, respectively).

Figure 8:
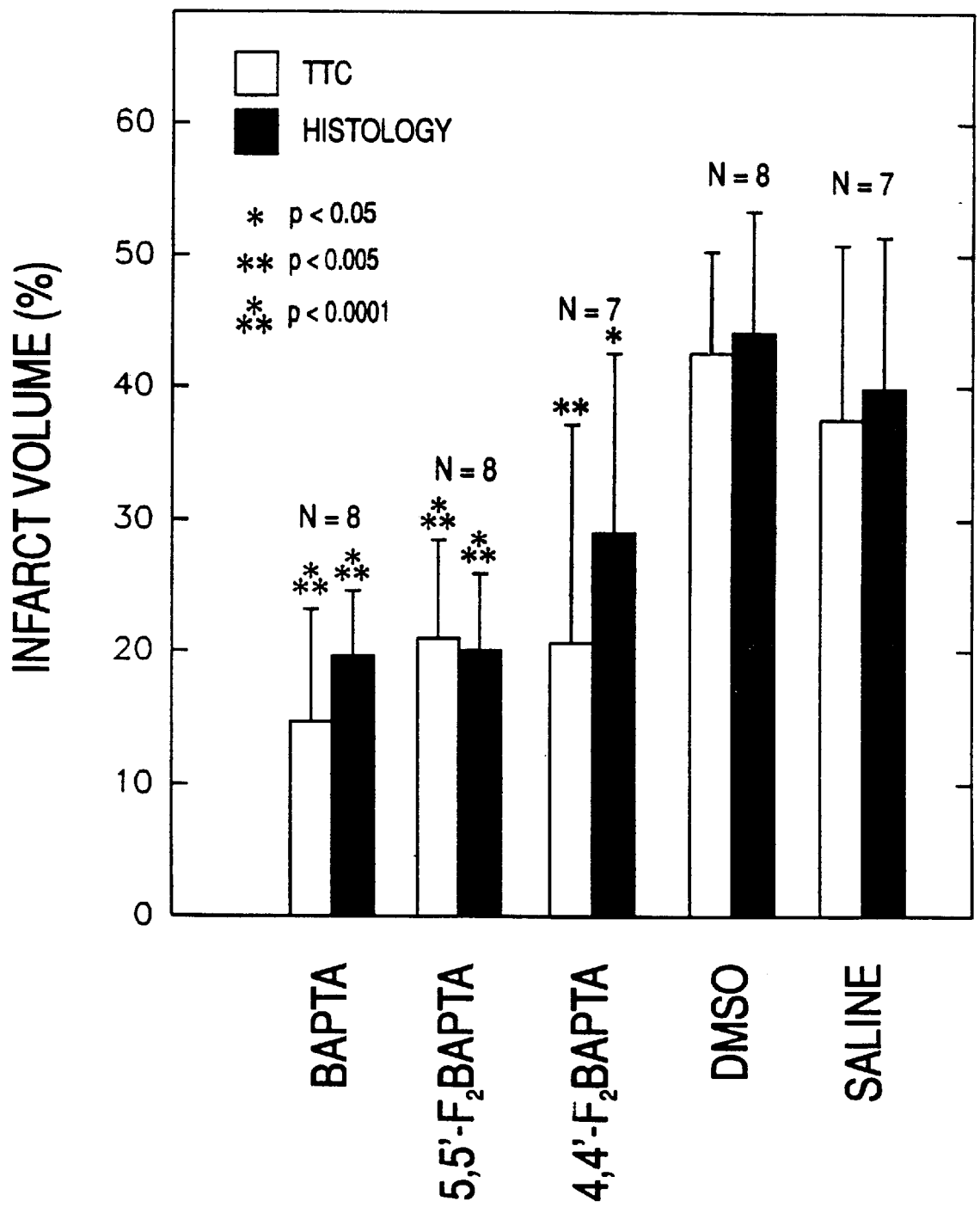
FIG. 8 represents a graph showing that in a second double-blinded randomized trial BAPTA-AM and its high $K_d$ (low $Ca^{2+}$-affinity) derivatives reduce the volume of infarction following focal cerebral ischemia. In a second randomized, double blinded, placebo controlled trial, pretreatment with BAPTA-AM ($K_d$ ca. 160 nM) reduced focal infarction volume by up to 66% as compared with controls. Results are shown as means ±standard deviations.

The second study in the same rat stroke model (see methods section), using BAPTA-AM, as well as 5,5'-$F_2$BAPTA-AM and 4,4'-$F_2$BAPTA-AM encompassed a total of 38 rats and 5 groups (7–8 rats per group). BAPTA and its derivatives 4,4'and 5,5'difluoro BAPTA were infused over fifty minutes into rats at a dosage of 18 mg per kg and 0.5 cc's of DMSO. To test whether infarctions produced in rats receiving DMSO alone were larger than usual, we added a group which received 0.5 ccs of saline, as a second control. FIG. 8 shows that rats treated with BAPTA-AM or its two derivatives had sustained substantially lower infarction volumes than either the DMSO or saline controls. The reduction in volume of infarction. stand from 50 percent with 4,4' and 5,5' difluoro BAPTA to 55 percent with BAPTA-AM alone, as compared with the DMSO alone groups. The results were statistically significant at p<0.05 for 4,4'$F_2$ BAPTA-AM and p<0.005 for BAPTA-AM and 5,5'$F_2$ BAPTA-AM.

We have further confirmed that the relationships observed between $Ca^{2+}$ buffering capacity and neuronal survival observed in the above tissue culture experiments (FIG. 4B) are reproduced in vivo. The importance of this lies in the fact that since equivalent neuroprotection is achieved with $Ca^{2+}$ buffers with low $Ca^{2+}$ affinity (high $K_d$), these agents are less likely to interfere with the normal functioning of neurons.

Example of a Pharmaceutical Composition according to the Invention

A solution of dimethylsulphoxide containing 1% w/v of BAPTA-AM was prepared by the dissolution of BAPTA-AM in dimethylsulphoxide solvent.

While the invention has been described in detail and with reference to specific embodiments thereof, it will be apparent to one skilled in the art that various changes and modifications can be made therein without departing from the spirit and scope of the invention.

We claim:

1. A method of reducing the damaging effect of an excitotoxic, ischemic or traumatic injury to cells in mammalian tissue of a host in vivo and treatment of epilepsy, said method comprising treating a host in need of such treatment with a non-toxic, damage-reducing effective amount of a cell membrane permeant calcium buffer which is a calcium ion chelating agent having a $K_D$ selected from the range $1 \times 10^{-4}$ to $1 \times 10^{-8}$ Molar.

2. A method as claimed in claim 1 wherein said cell membrane permeant buffer is a compound having the generic formula:

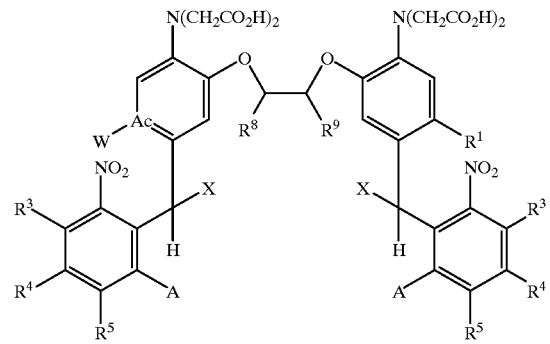

and the pharmaceutically acceptable nontoxic salts and esters thereof wherein:

A is —$NO_2$ or —H;

$R^1$ is selected from the group consisting of —H, $R^3$, $R^4$ and $R^5$ are independently —H, OH, $NR^6R^7$, or alkoxy, or $R^3$ and $R^4$ together are —$OCH_2O$— or —$OCH_2CH_2O$— and $R^5$ is —H, OH, $NR^6R^7$, or alkoxy, or $R^4$ and $R^5$ together are —$OCH_2O$— or $OCH_2CH_2O$— and $R^3$ is —H, OH, $NR^6R^7$, or alkoxy;

X is selected from the group consisting of —OH, alkoxy, —Cl, Br, —NR⁶R⁷, —OCOCH₃, —OCOCF₃, —OCOCH₂NH₂, —OPO₃H, and —OSO₂CH₃;

R⁶ and R⁷ are independently —H, methyl or ethyl;

R⁸ and R⁹ are independently —H, —CH₃, —C₂H₅, or —CH₂OH except that both may not be —H simultaneously; or R⁸ and R⁹ together are —(CH₂)ₘ—Y—(CH₂)ₙ— where m and n are independently 1 or 2 and Y is selected from the group consisting of —CH₂—, —O—, —NR⁶—, —S—, and —S—S—; and W is —H, —OH, or —NHR⁶.

3. A method as claimed in claim 1 wherein said cell membrane permeant buffer is a compound having the generic formula:

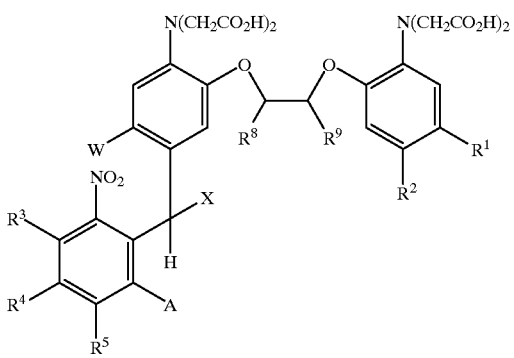

and the pharmaceutically acceptable non-toxic salts and esters thereof wherein:

A is —NO₂ or —H;

R³, R⁴ and R⁵ are independently —H, OH, NR⁶R⁷, or alkoxy, or

R³ and R⁴ together are —OCH₂O— or —OCH₂CH₂O— and R⁵ is —H, OH, NR⁶R⁷, or alkoxy, or R⁴ and R⁵ together are —OCH₂O— or —OCH₂CH₂O— and R³ is —H, OH, NR⁶R⁷, or alkoxy;

X is selected from the group consisting of OH, alkoxy, —Cl, —Br, —NR⁶R⁷, —OCOCH₃, —OCOCF₃, —OCOCH₂NH₂, —OPO₃H, and —OSO₂CH₃;

R⁶ and R⁷ are independently —H, methyl or ethyl;

R⁸ and R⁹ are independently —H or —CH₃, or —C₂H₅ or —CH₂OH except that both may not be —H simultaneously; or R⁸ and R⁹ together are —(CH₂)ₘ—Y—(CH₂)ₙ— where m and n are independently, 1 or 2 and Y is selected from the group consisting of —CH₂—, —O—, —NR⁶—, —S—, and —S—S—; and W is —H, —OH, or —NHR⁶.

4. A method as claimed in claim 1 wherein said cell membrane permeant buffer is a compound having the generic formula:

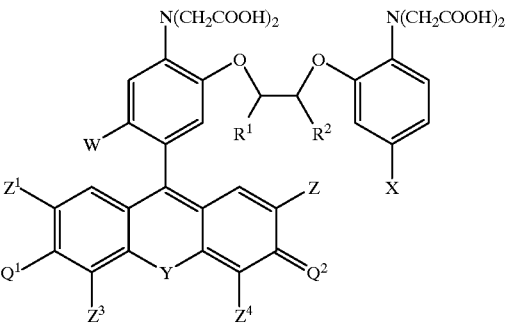

and the pharmaceutically acceptable non-toxic salts and esters thereof wherein:

E¹ and E² are independently H, CH₃ C₂H₅, CH₂OH, COOH, or CH₂COOH, or E¹ and E² together are —(CH₂)m—V—(CH₂)ₙ— where m and n are independently 1 or 2 and V is selected from the group consisting of —CH₂—, —O—, NH—, —NMc—, —S—, and —S—S—;

W is H, OH, or COOH;

X is H, Me, COOH, F, Cl, Br, I or NO₂

Y is —O—, —NMe—, —S—, —CH₂—, —CMe₂—, —CF₂—, or a direct sigma bond making a five-membered central ring;

Z¹, Z², Z³, and Z⁴ are independently H, F, Cl, Br, I, or Me, and Q¹, Q² equal R₁R₂N—, or HO—, O=, where R¹ and R₂ are independently selected from the group consisting of H, Me, and Et; or Z¹, Q¹, or Z³ together are

—(CH₂)₃—N—(CH₂)₃ and

Z², Q², Z⁴ together are —(CH₂)₃—N—(CH₂)₃—.

5. A method as claimed in claim 1 wherein said cell membrane permeant buffer is a compound having the generic formula:

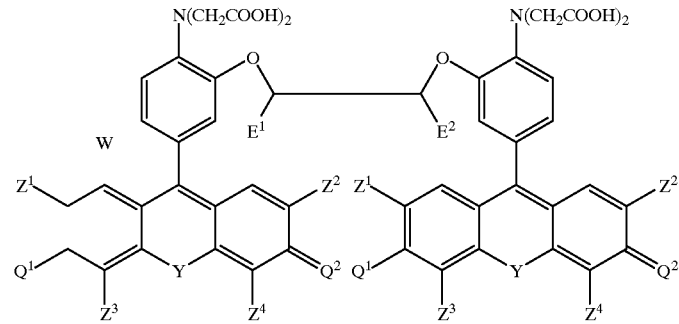

and the pharmaceutically acceptable non-toxic salts and esters thereof wherein:

$E^1$ and $E^2$ are independently H, $CH_3$, $C_2H_5$, $CH_2OH$, COOH, or $CH_2COOH$, or E1 and $E^2$ together are —$(CH_2)_m$—V—$(CH_2)_n$— where m and n are independently 1 or 2 and V is selected from the group consisting of $CH_2$—, —O—, —NH—, —NMe—, —S—, and —S—S—;

W is H, OH, or COOH;

X is H, Me, COOH, F, Cl, Br, I, or $NO_2$;

Y is —O—, —NMe—, —S—, —$CH_2$—, —$CMe_2$—, —$CF_2$—, —CO.— or a direct sigma bond making five-membered central ring;

$Z^1, Z^2, Z^3$, and $Z^4$ are independently H, F, Cl, Br, I, or Me, and $Q^1, Q^2$ equal $R_1R_2N$—, or HO—, O= or $R_1R_2N$—, O—, where $R^1$ and $R_2$ are independently selected from the group consisting of H, Me, and Et; or $Z^1, Q^1, Z^3$ together are

—$(CH_2)_3$—N—$(CH_2)_3$— and $Z^2, Q^2, Z^4$ together are

—$(CH_2)_3$—N—$(CH_2)_3$—.

6. A method as claimed in claim 1 wherein said cell membrane permeant buffer is a compound having the generic formula:

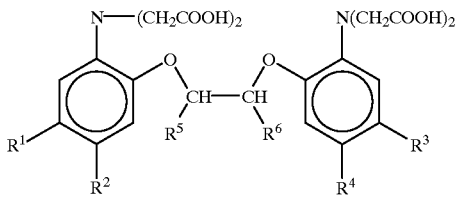

and the salts or the non-polymeric esters thereof wherein $R^1$ and $R^3$ are each independently selected from —H, OH, —$CH_3$, —F, Cl, —Br, —I, —COOH. —CN, —$NO_2$ or —$NHR^7$ wherein $R^7$, is independently selected from —H, methyl or ethyl;

$R^2$ is —(C=O)$CR^8$—N—N, wherein $R^8$ is independently selected from —H, C1–C4 alkyl, phenyl, —COOH, —$COOR^7$ —(C—O)$CH_3$, or —CF3 wherein $R_7$ is defined hereinabove;

$R^4$ is independently selected from $R^2$, —H, —$CH_3$, —$CH_2CH_3$, —F, —Cl—, —Br, —I, —COOH, —CN or —$NO_2$;

$R^5$ and $R^6$ are each independently selected from —H, —$CH_3$, —$C_2H_5$, phenyl, or —$CH_2OH$, or $R^5$ and $R^6$ together form —$(CH_2)_m$—Y—$(CH_2)_n$— where m and n are each independently 1 or 2, and Y is selected from —$CH_2$—, —O—, —$NHR^7$, —S— or —S—S—, wherein $R^7$ is defined hereinabove.

7. A method as claimed in claim 1 wherein said cell membrane permeant buffer is selected from the group consisting of BAPTA-AM; EGTA-AM; 5,5' dibromo BAPTA-AM; 5,5' difluoro BAPTA-AM; and 4,4'-difluoro BAPTA-AM.

8. A method as claimed as claimed in claim 1 wherein said injury is caused by a reduction in blood flow, oxygen flow or nutrient flow, or trauma, radiation, toxin exposure, infection, neoplasia degenerative processes, or inflammation, to said tissue.

9. A method as claimed in claim 1 wherein said injury is cerebral ischemia.

10. A method as claimed in claim 1 wherein said mammalian tissue comprises mammalian cells of the heart, liver, spleen, gastrointestinal tract, vascular smooth muscle and the nervous system.

11. A method as claimed in claim 1 wherein said cells in mammalian tissue are treated with a prophylactic amount of cell membrane permeant calcium buffer prior to the occurrence of said injury to said cells.

12. A method as claimed in claim 1 wherein said cell membrane permeant calcium buffer is administered to said cells after said mammaliah tissue has sustained said injury.

13. A method as claimed in claim 1 wherein said cell membrane permeant calcium buffer is administered to said mammal intravenously, intrathecally, intracisternally, intraventricularly, topically, sub-cutaneously, by ingestion and by intramuscular injection.

14. A method of controlling the concentration of $Ca^{2+}$ ions in the vicinity of ion channel pores of cells in vivo to prevent the diffusion of toxic amounts of said $Ca^{2+}$ ions to subcellular sites located near the source of $Ca^{2+}$ influx to prevent the triggering of neurotoxic phenomena, said method comprising administering an effective, non-toxic amount of a membrane permeant $Ca^{2+}$ buffer to said cell in vivo.

15. A method as claimed in claim 14 wherein said cell membrane permeant buffer is a calcium ion chelating agent having a $K_D$ selected from the range $1\times10^{-4}$ to $1\times10^{-8}$ Molar.

16. A method as claimed in claim 14 wherein said cell membrane permeant buffer is selected from the group consisting of BAPTA-AM; EGTA-AM; 5,5' dibromo BAPTA-AM; 5,5' difluoro BAPTA-AM; and 4,4'-difluoro BAPTA-AM.

* * * * *